(12) United States Patent
Sato et al.

(10) Patent No.: US 8,735,598 B2
(45) Date of Patent: May 27, 2014

(54) METHOD FOR PRODUCING 1-BIPHENYLMETHYLIMIDAZOLE COMPOUND

(75) Inventors: Koji Sato, Tokyo (JP); Tsutomu Yagi, Tokyo (JP); Kenji Sakuratani, Tokyo (JP); Yuichiro Tani, Tokyo (JP)

(73) Assignee: Daiichi Sankyo Company, Limited, Tokyo (JP)

( * ) Notice: Subject to any disclaimer, the term of this patent is extended or adjusted under 35 U.S.C. 154(b) by 632 days.

(21) Appl. No.: 12/996,697

(22) PCT Filed: Jun. 8, 2009

(86) PCT No.: PCT/JP2009/060419
§ 371 (c)(1),
(2), (4) Date: Dec. 30, 2010

(87) PCT Pub. No.: WO2009/151016
PCT Pub. Date: Dec. 17, 2009

(65) Prior Publication Data
US 2011/0092713 A1   Apr. 21, 2011

(30) Foreign Application Priority Data
Jun. 9, 2008   (JP) ................................ 2008-150686

(51) Int. Cl.
*C07C 67/313* (2006.01)
*C07D 233/90* (2006.01)
*C07D 403/10* (2006.01)
*C07D 405/14* (2006.01)

(52) U.S. Cl.
USPC .......................... 548/334.5; 548/253; 560/176

(58) Field of Classification Search
USPC ................. 548/334.5, 253; 560/176
See application file for complete search history.

(56) References Cited

U.S. PATENT DOCUMENTS

| | | | |
|---|---|---|---|
| 5,616,599 A | 4/1997 | Yanagisawa et al. | |
| 5,646,171 A | 7/1997 | Yanagisawa et al. | |
| 5,744,612 A | 4/1998 | Koguro et al. | |
| 6,040,454 A | 3/2000 | Koguro et al. | |
| 7,528,258 B2 | 5/2009 | Hedvati et al. | |
| 7,563,814 B2 | 7/2009 | Hedvati et al. | |
| 8,048,904 B2 | 11/2011 | Ramanjaneyulu et al. | |
| 8,076,492 B2 | 12/2011 | Pathi et al. | |
| 2006/0069141 A1 | 3/2006 | Hedvati et al. | |
| 2006/0074117 A1 | 4/2006 | Hedvati et al. | |
| 2006/0149078 A1 | 7/2006 | Hedvati et al. | |
| 2007/0054948 A1 | 3/2007 | Hedvati et al. | |
| 2008/0076932 A1 | 3/2008 | Razzetti et al. | |
| 2009/0281327 A1 | 11/2009 | Ramanjaneyulu et al. | |
| 2010/0076200 A1 | 3/2010 | Hedvati et al. | |

FOREIGN PATENT DOCUMENTS

| | | |
|---|---|---|
| CN | 1976926 A | 6/2007 |
| CN | 1993355 A | 7/2007 |
| CN | 101094850 A | 12/2007 |
| CN | 101238119 A | 8/2008 |
| EP | 0 796 852 A1 | 9/1997 |
| EP | 0 503 785 B1 | 4/2001 |
| EP | 2036904 A1 | 3/2009 |
| JP | 7-121918 | 12/1995 |
| JP | 7-121918 B | 12/1995 |
| JP | 3521304 B2 | 4/2004 |
| JP | 3671266 B2 | 4/2004 |
| JP | 2004-217542 A | 8/2004 |
| JP | 2006-111586 A | 4/2006 |
| JP | 2007-509992 | 4/2007 |
| JP | 2007-509993 | 4/2007 |
| JP | 2007-526342 | 9/2007 |
| JP | 2008-088172 | 4/2008 |
| WO | WO 2006/029056 | 3/2006 |
| WO | WO 2006/029057 | 3/2006 |
| WO | WO 2006/073519 | 7/2006 |
| WO | 2007017135 A2 | 2/2007 |
| WO | WO 2007-047838 A2 | 4/2007 |
| WO | WO 2007/048361 | 5/2007 |
| WO | WO 2007/148344 | 12/2007 |
| WO | WO 2008/043996 | 4/2008 |

(Continued)

OTHER PUBLICATIONS

International Search Report for International Application No. PCT/JP2009/060419, mailed on Aug. 11, 2009 (English & Japanese).

(Continued)

*Primary Examiner* — Kamal Saeed
(74) *Attorney, Agent, or Firm* — Locke Lord, LLP

(57) ABSTRACT

The present invention provides a method for producing a 1-biphenylmethylimidazole compound having superior angiotensin II receptor antagonistic activity, or an intermediate thereof.

The present invention provides a method for producing a compound having the formula (5) ($R^1$, $R^a$: H, an alkyl group) by oxidizing a compound having the formula (1) ($R^a$: H, an alkyl group) using an oxidizing agent in the presence of a radical initiation reagent, and then reacting with an ammonia-generating reagent and a compound having the formula $R^1CHO$ ($R^1$: H, an alkyl group) or a compound having the formula $R^1C(OR^b)_3$ ($R^1$: H, an alkyl group; $R^b$: an alkyl group).

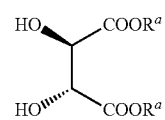

(1)

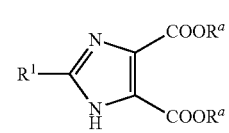

(5)

31 Claims, No Drawings

(56) References Cited

FOREIGN PATENT DOCUMENTS

| WO | WO 2009/019304 | 2/2009 |
| WO | WO 2010/026255 | 3/2010 |
| WO | WO 2011/014611 | 2/2011 |
| WO | WO 2012/001694 | 1/2012 |

OTHER PUBLICATIONS

International Preliminary Examination Report on Patentability for International Application No. PCT/JP2009/060419, issued on Dec. 13, 2010 and the English translation issued on Jan. 11, 2011.
Written Opinion of the International Searching Authority for International Application No. PCT/JP2009/060419, mailed on Aug. 11, 2009 (English & Japanese).
Yanagisawa, H. et al., "Nonpeptide Angiotensin II Receptor Antagonists: Synthesis, Biological Activities, and Structure—Activity Relationships of Imidazole-5-carboxylic Acids Bearing Alkyl, Alkenyl, and Hydroxyalkyl Substituents at the 4-Position and Their Related Compounds", *J. Med. Chem.*, vol. 39, pp. 323-338, 1996.
Jitender M. Khurana et al., "A Novel Method of Synthesis of 1,2-diketones from 1,2-diols Using N-bromosuccinimide", Tetrahedron Letters vol. 44, No. 26, Jun. 23, 2003, pp. 4909-4212.
European Search Report dated Aug. 29, 2011 to corresponding European Application No. EP 09 76 2446.
Hiroyuki Koike, et al. "Olmesartan Medoxomil, a Novel Potent Angiotensin II Blocker." *Annu. Rep. Sankyo Res. Lab.* 55:1-91 (2003).
P. Marceau, et al. "Graphite intercalation compounds as precursors of activated metals. II *. Synthesis of beta, gamma-unsaturated ketones through condensation of allylic organozinc derivatives with nitriles." *Journal of Organometallic Chemistry*, 403:21-27 (1991).
Adam Shih-Yuan Lee, et al. "Synthesis of allyl ketone via Lewis acid promoted Barbier-type reaction." *Tetrahedron Letters*, 41:8803-8806 (2000).
Yasunobu Akiyama, et al. "Reaction of organocadmium reagents with ethyl cyanoformate: preparation of alpha-keto esters." *Chemistry Letters*, 1231-1232 (1983).
U.S. Appl. No. 13/266,967, filed Nov. 8, 2011, Hiroshi Kiyota.
U.S. Appl. No. 13/266,885, filed Nov. 17, 2011, Shigeo Yanagihara.
Yanagisawa, H, "Nonpeptide Angiotensin II Receptor Antagonists: Synthesis, Biological Activities, and Structure-Activity Relationships of Imidazole-5-carboxylic Acids Bearing Alkyl, Alkenyl, and Hydroxyalkyl Substituents at the 4-Position and Their Related Compounds", J. Med. Chem., 39, 323-338 (1996).
Office Action issued in Colombian Application No. 11161167; dated Aug. 28, 2013.
International Preliminary Report on Patentability, issued in PCT/JP2010/057403, mailed Nov. 9, 2011.
International Search Report, issued in PCT/JP2010/057403, mailed Jun. 8, 2010.
Written Opinion of the International Searching Authority, issued in PCT/JP2010/057403, mailed Jun. 8, 2010.
International Preliminary Report on Patentability, issued in PCT/JP2010/057404, mailed Nov. 9, 2011.
International Search Report, issued in PCT/JP2010/057404, mailed Jun. 8, 2010.
Written Opinion of the International Searching Authority, issued in PCT/JP2010/057404, mailed Jun. 8, 2010.
Supplementary European Search Report, issued in EP Application No. 10769711.2, mailed Sep. 6, 2012.
Supplementary European Search Report, issued in EP Application No. 10769712.0, mailed Aug. 24, 2012.
English Translation of Opposition filed by Tecnoquimicas S.A., against Colombia App. No. 11-161167, Gazette 647, Publication No. 817, Jun. 29, 2012.
English Translation of Defense of Opposition by Tecnoquimicas S.A., against Colombia App. No. 11-161167, Gazette 647, Publication No. 817, Jun. 29, 2012.
English Translation of Opposition filed by Laboratorio Franco Colombiano S.A.S. Lafrancol S.A.S., against Colombia App. No. 11-161167, Gazette 647, Publication No. 817, Jun. 29, 2012.
Giron, D., Technochimica acta 248-1-59, Elsevier Science B.V., 1995, pp. 3 to 11.
J. Garrido, Form and Structure of Crystals, (op. cit.), chapter V, pp. 204, 212 (with English translation), 1973.
A.R. Verma, P. Krishna—"Polytypism in crystals", John Wiley and Son Inc., New York 1966.
Vila Jato J.L. Technologia Farmaceutica, vol. 1, pp. 42 to 49 (1997) (cited at pp. 3, 4 of English translation of Colombia opposition filed by Tecnoquimicas S.A.
Doelker E. Crystalline modifications and polymorphism changes during drug manufacture, Ann Pharm Fr. May 2002; 60(3): 161-76 (with English abstract).
The Merck Index. "An encyclopedia of chemicals, drugs, and biological. Fourteenth Edition." 2006. p. 1178. (Olmesartan).
EPO Third Party Observation, filed Sep. 21, 2012 against EPA No. 10769712.0.
Office Action and Search Report issued in Chinese Application No. 2010800189009; dated Jul. 31, 2013.
Office Action and Search Report issued in Chinese Application No. 2010800188970; dated Aug. 12, 2013.

METHOD FOR PRODUCING 1-BIPHENYLMETHYLIMIDAZOLE COMPOUND

This application is a national phase entry under 35 U.S.C. §371 of International Application Number PCT/JP2009/060419, filed on Jun. 8, 2009, entitled "METHOD FOR PRODUCING 1-BIPHENYLMETHYLIMIDAZOLE COMPOUND", which claims the benefit of Japanese Patent Application Number JP 2008-150686, filed on Jun. 9, 2008, all of which are hereby incorporated by reference.

FIELD OF THE INVENTION

The present invention relates to a novel method for producing a 1-biphenylmethylimidazole compound [preferably the following Compound (13a)] having a superior angiotensin II receptor antagonistic activity, or an intermediate thereof.

BACKGROUND

Method V (see Non-patent reference 1) or Method W (see Example 79 of Patent reference 1) is known as a method for producing a 1-biphenylmethylimidazole compound having an angiotensin II receptor antagonistic activity.

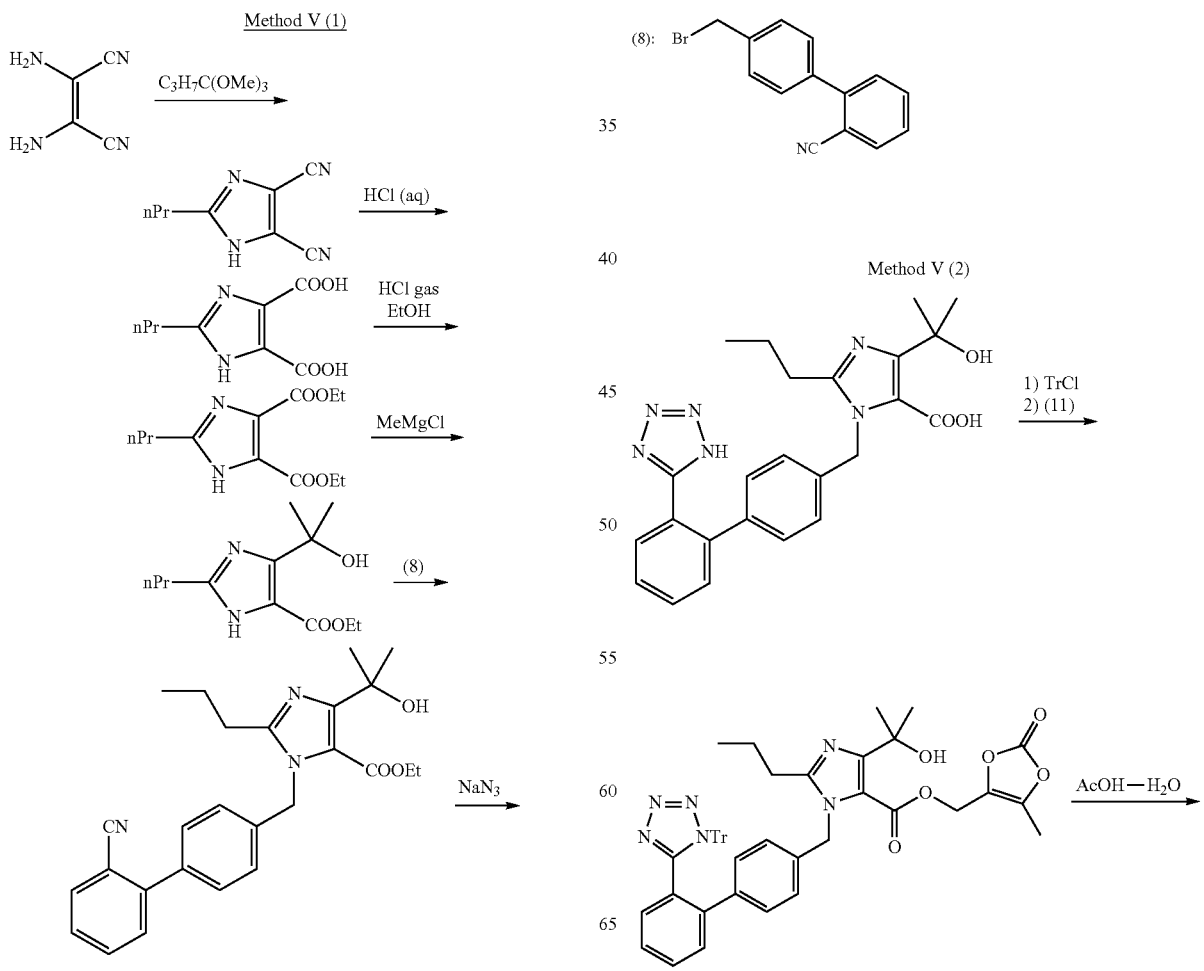

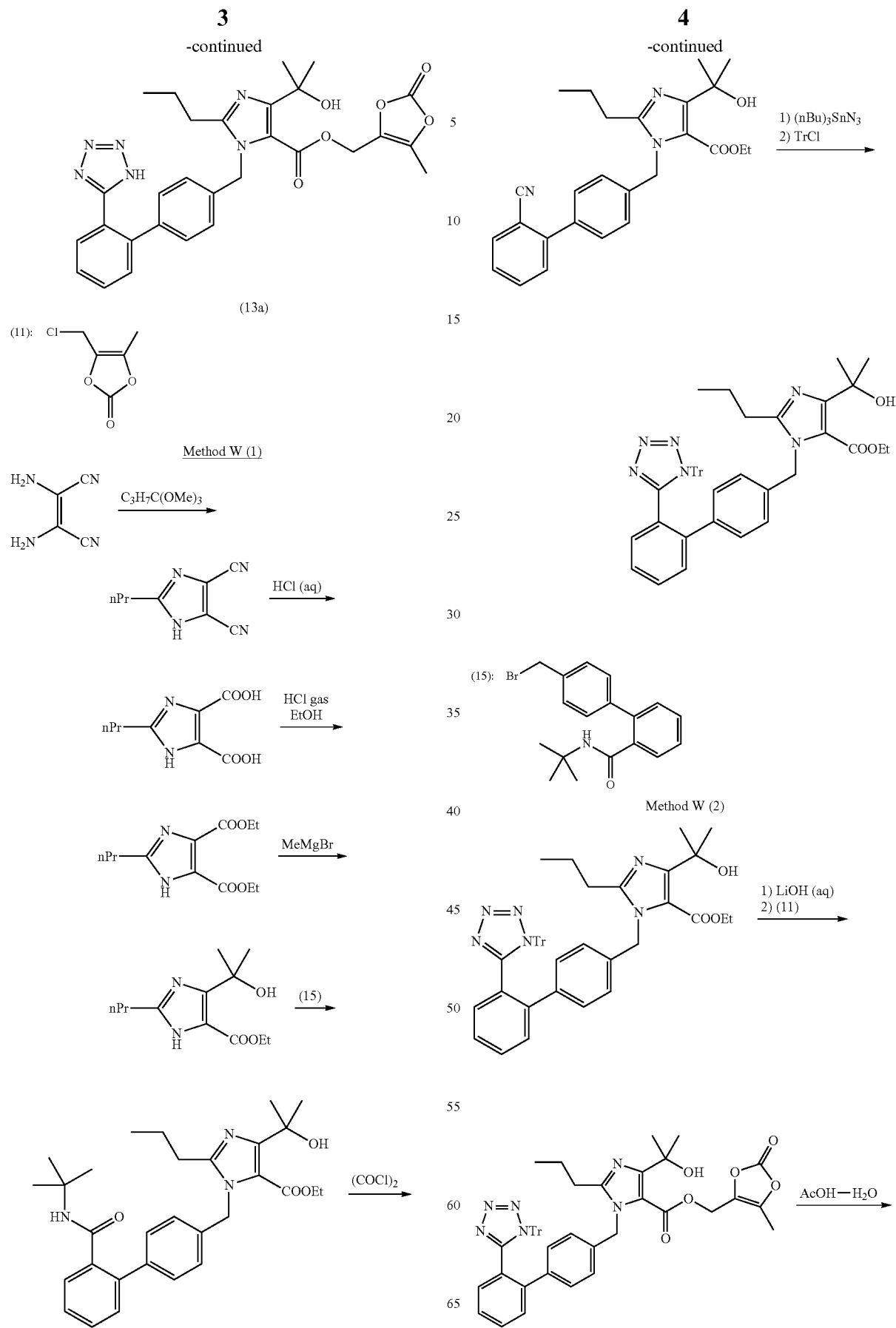

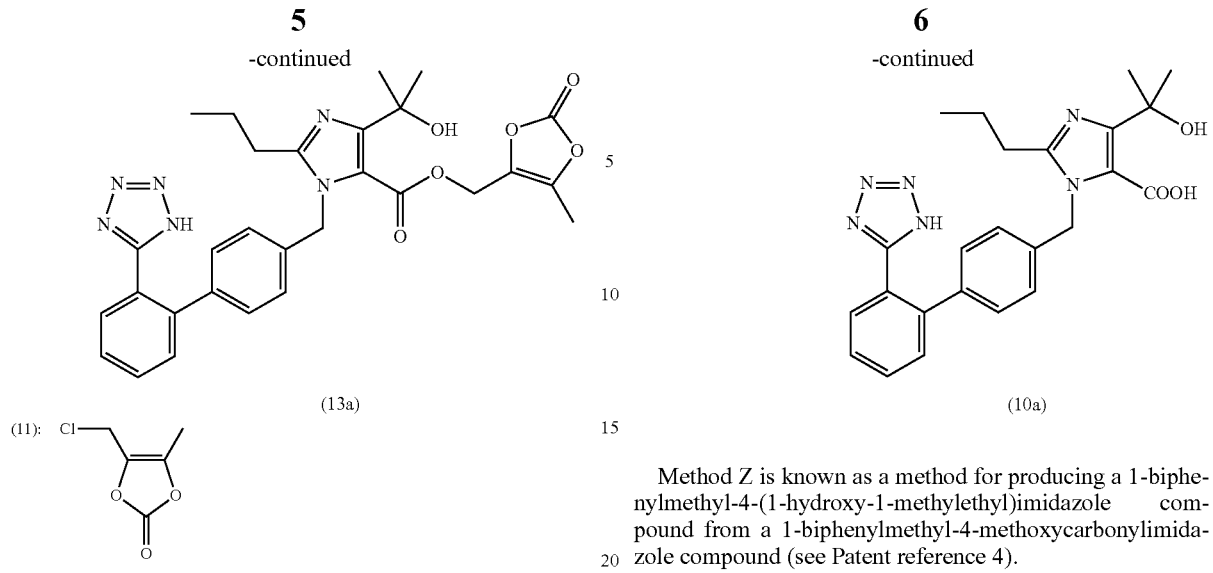

Method X is known as a method for producing an imidazole compound using tartaric acid diester (see Patent reference 2).

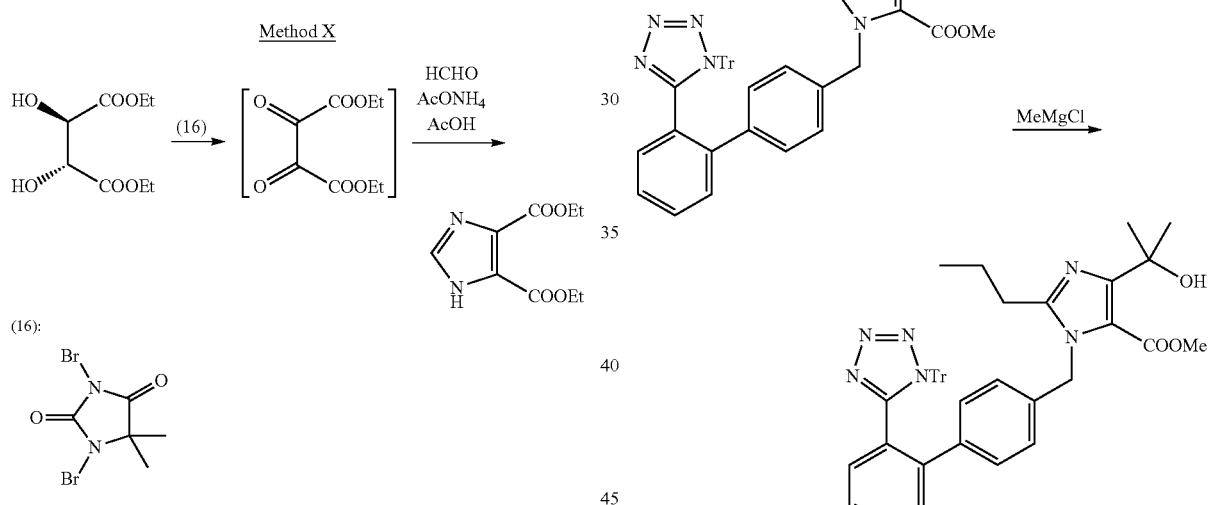

Method Y is known as a method for producing a 1-(tetrazolylbiphenylmethyl)imidazole compound from a 1-(cyanobiphenylmethyl)imidazole compound (see Patent reference 3).

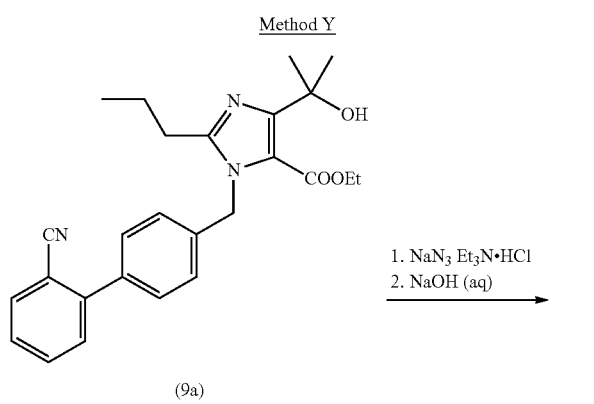

Method Z is known as a method for producing a 1-biphenylmethyl-4-(1-hydroxy-1-methylethyl)imidazole compound from a 1-biphenylmethyl-4-methoxycarbonylimidazole compound (see Patent reference 4).

From an industrial viewpoint, a production method is desired which is superior in that the reaction proceeds efficiently in an industrial reaction vessel such as a reactor; that it has high total yield; that it has high reaction selectivity; that it provides the desired compound with high purity; that it has a small number of reaction steps; that the reaction is safe; and the like.

PRIOR ART REFERENCES

Patent References

Patent reference 1: JP (Toku-Kou-Hei) 7-121918 (the corresponding U.S. Pat. No. 5,616,599)
Patent reference 2: JP (Toku-Kai) 2004-217542
Patent reference 3: JP 3521304
Patent reference 4: International patent publication pamphlet WO 2007/047838

Non-Patent Reference

Non-patent reference 1: Annual Report of Sankyo Research Laboratories, 2003, vol. 55, p. 1-91

SUMMARY OF THE INVENTION

Object of the Invention

As a result of conducting extensive studies on a method for producing a 1-biphenylmethylimidazole compound [preferably the following Compound (13a)] or an intermediate thereof, the inventors of the present invention found that the novel production method of the present invention is superior to known production methods from an industrial viewpoint. The present invention was completed on the basis of the above findings.

Means for Achieving the Object

The present invention provides a novel method for producing a 1-biphenylmethylimidazole compound [preferably the following Compound (13a)] having a superior angiotensin II receptor antagonistic activity, or an intermediate thereof. The production method of the present invention is indicated by the following Method A [Method A(1) and Method A(2)] or Method B.

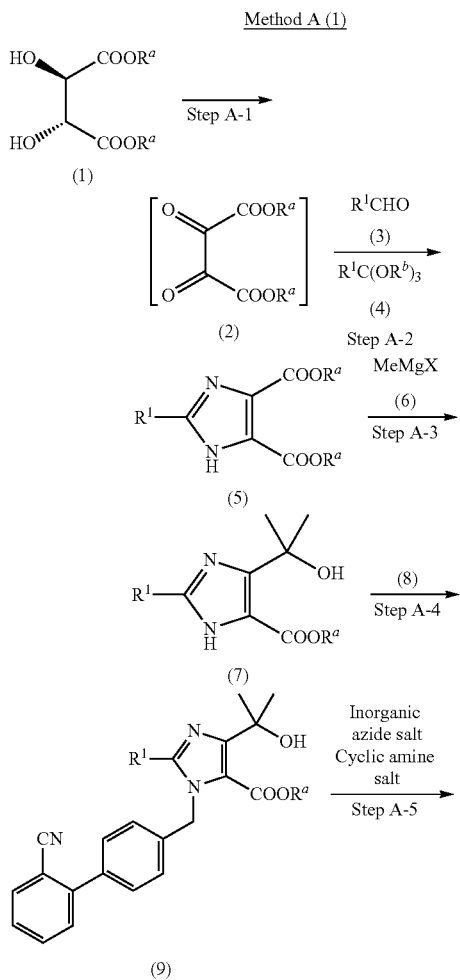

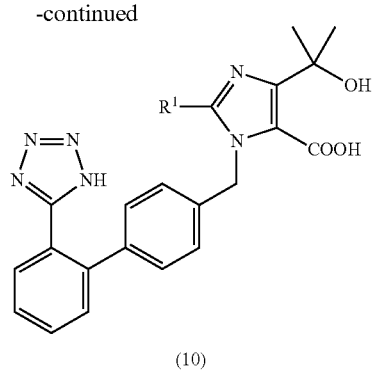

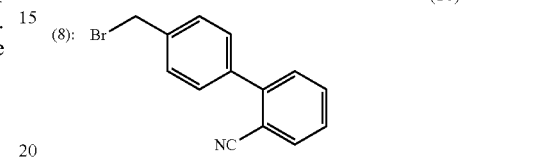

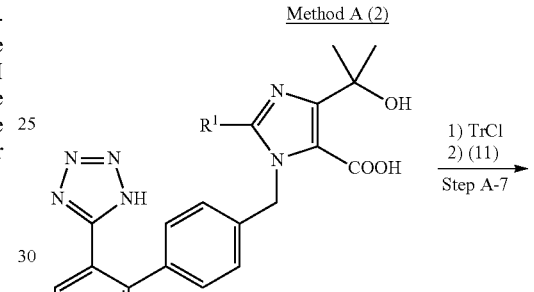

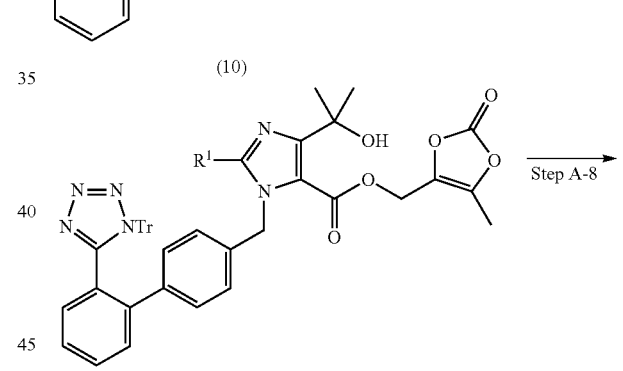

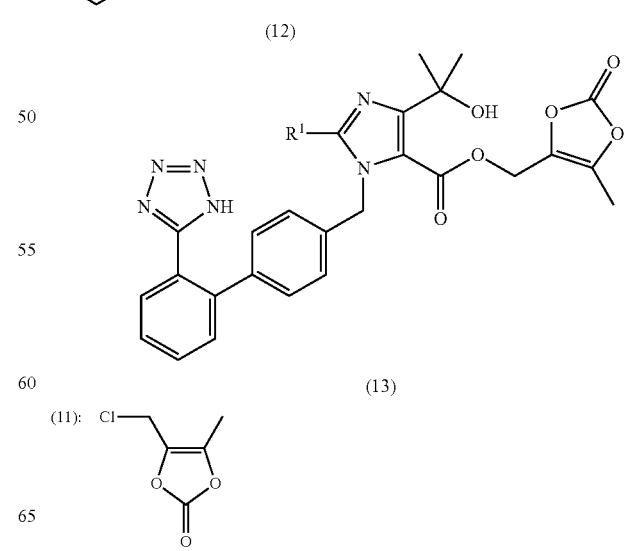

-continued

Method B

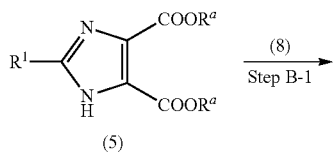

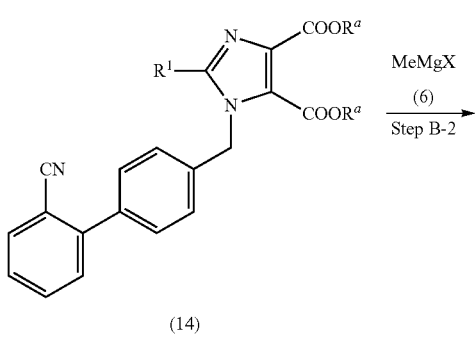

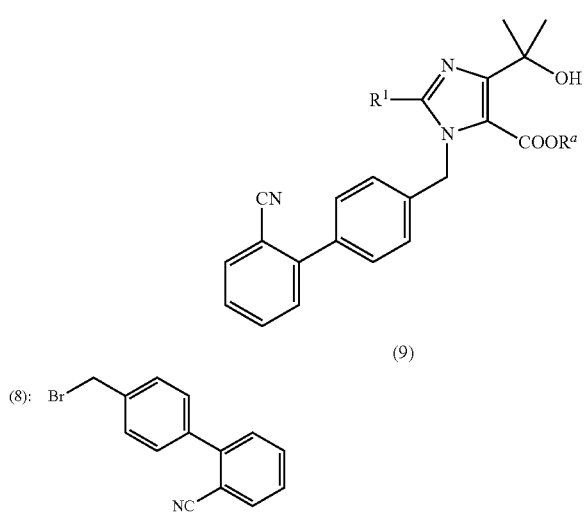

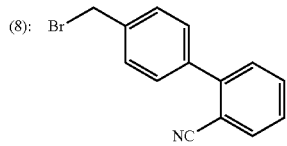

In the present invention, $R^1$ represents a $C_1$-$C_4$ alkyl group, $R^a$ represents a $C_1$-$C_4$ alkyl group, $R^b$ represents a $C_1$-$C_6$ alkyl group, X represents a chloro group, a bromo group or an iodo group, and Tr represents a triphenylmethyl group.

In one aspect thereof, the present invention provides the inventions of [1] to [33] described below:

[1] A method for producing a compound having the following formula (5):

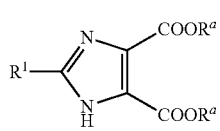

(wherein $R^1$ represents a hydrogen atom or a $C_1$-$C_4$ alkyl group, and $R^a$ represents a hydrogen atom or a $C_1$-$C_4$ alkyl group)

by oxidizing a compound having the following formula (1):

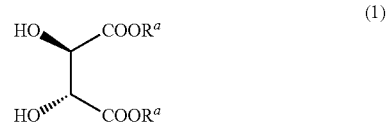

(wherein $R^a$ represents a hydrogen atom or a $C_1$-$C_4$ alkyl group) using an oxidizing agent in the presence of a radical initiation reagent, and then reacting the resulting compound with an ammonia-generating reagent and a compound having the formula $R^1$CHO (wherein $R^1$ represents a hydrogen atom or a $C_1$-$C_4$ alkyl group) or a compound having the formula $R^1$C(OR$^b$)$_3$ (wherein $R^1$ represents a hydrogen atom or a $C_1$-$C_4$ alkyl group, and $R^b$ represents a $C_1$-$C_6$ alkyl group);

[2] The production method according to [1], wherein $R^1$ is a 1-propyl group and the compound having the formula $R^1$CHO is used;

[3] The production method according to [1] or [2], wherein $R^a$ is an ethyl group;

[4] The production method according to any one of [1] to [3], wherein the radical initiation reagent is an azobis compound;

[5] The production method according to any one of [1] to [3], wherein the radical initiation reagent is 2,2'-azobis(4-methoxy-2,4-dimethylvaleronitrile);

[6] The production method according to any one of [1] to [5], wherein the oxidizing agent is a halogenosuccinimide compound or a dihalogenohydantoin compound;

[7] The production method according to any one of [1] to [5], wherein the oxidizing agent is 1,3-dibromo-5,5-dimethylhydantoin;

[8] The production method according to any one of [1] to [7], wherein the ammonia-generating reagent is an ammonium salt;

[9] The production method according to any one of [1] to [7], wherein the ammonia-generating reagent is ammonium acetate;

[10] The production method according to any one of [1] to [9], wherein the reaction is carried out under light-shielding conditions;

[11] The production method according to [1], wherein $R^1$ is a 1-propyl group, $R^a$ is an ethyl group, the radical initiation reagent is an azobis compound, the oxidizing agent is a halogenosuccinimide compound or a dihalogenohydantoin compound, the ammonia-generating reagent is an ammonium salt, and the compound having the formula $R^1$CHO is used;

[12] The production method according to [1], wherein $R^1$ is a 1-propyl group, $R^a$ is an ethyl group, the radical initiation reagent is 2,2'-azobis(4-methoxy-2,4-dimethylvaleronitrile), the oxidizing agent is 1,3-dibromo-5,5-dimethylhydantoin, the ammonia-generating reagent is ammonium acetate, the compound having the formula $R^1$CHO is used, and the reaction is carried out under light-shielding conditions;

[13] A method for producing a compound having the formula (2):

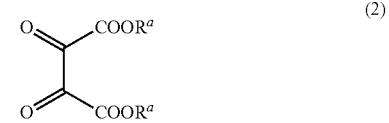

(wherein $R^a$ represents a hydrogen atom or a $C_1$-$C_4$ alkyl group)

by oxidizing a compound having the formula (1):

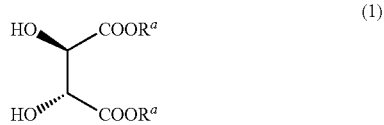

(wherein $R^a$ represents a hydrogen atom or a $C_1$-$C_4$ alkyl group) using an oxidizing agent in the presence of a radical initiation reagent;

[14] The production method according to [13], wherein $R^a$ is an ethyl group, the radical initiation reagent is an azobis compound, and the oxidizing agent is a halogenosuccinimide compound or a dihalogenohydantoin compound;

[15] The production method according to [13], wherein $R^a$ is an ethyl group, the radical initiation reagent is 2,2'-azobis(4-methoxy-2,4-dimethylvaleronitrile), the oxidizing agent is 1,3-dibromo-5,5-dimethylhydantoin, and the reaction is carried out under light-shielding conditions;

[16] A method for producing a compound having the formula (10a):

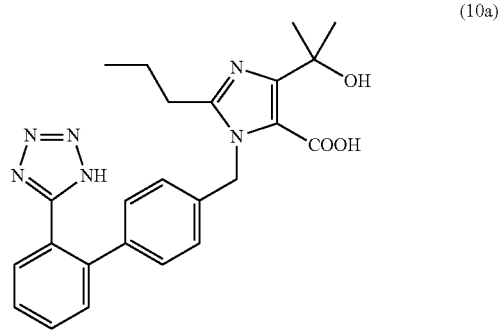 [SMILES: CCCc1nc(C(C)(C)O)c(C(=O)O)n1Cc1ccc(-c2ccccc2-c2nnn[nH]2)cc1]

by reacting a compound having the formula (9b):

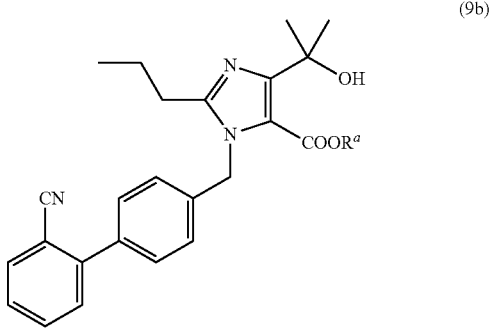

(wherein $R^a$ represents a hydrogen atom or a $C_1$-$C_4$ alkyl group) with an inorganic azide salt having the formula $M(N_3)_n$ (wherein M represents an alkali metal or an alkaline earth metal, and n represents 1 or 2) in an aromatic hydrocarbon in the presence of a cyclic amine salt, and hydrolyzing the resulting compound;

[17] The production method according to [16], wherein $R^a$ is an ethyl group;

[18] The production method according to [16] or [17], wherein the inorganic azide salt is sodium azide;

[19] The production method according to any one of [16] to [18], wherein the cyclic amine salt is a hydrochloride or a hydrobromide of N-methylpyrrolidine, N-methylpiperidine, N,N-dimethylpiperazine, N-methylmorpholine, N-methylthiomorpholine, N-methylhomopiperidine or N,N-dimethylhomopiperazine;

[20] The production method according to any one of [16] to [18], wherein the cyclic amine salt is a hydrochloride or a hydrobromide of N-methylpiperidine, N,N-dimethylpiperazine, N-methylmorpholine or N-methylthiomorpholine;

[21] The production method according to any one of [16] to [18], wherein the cyclic amine salt is N-methylpiperidine hydrochloride, N,N-dimethylpiperazine dihydrochloride or N-methylmorpholine hydrochloride;

[22] The production method according to [16], wherein $R^a$ is an ethyl group, the inorganic azide salt is sodium azide, and the cyclic amine salt is a hydrochloride or a hydrobromide of N-methylpyrrolidine, N-methylpiperidine, N,N-dimethylpiperazine, N-methylmorpholine, N-methylthiomorpholine, N-methylhomopiperidine or N,N-dimethylhomopiperazine;

[23] The production method according to [16], wherein $R^a$ is an ethyl group, the inorganic azide salt is sodium azide, and the cyclic amine salt is N-methylpiperidine hydrochloride, N,N-dimethylpiperazine dihydrochloride or N-methylmorpholine hydrochloride;

[24] A method for producing a compound having the formula (9):

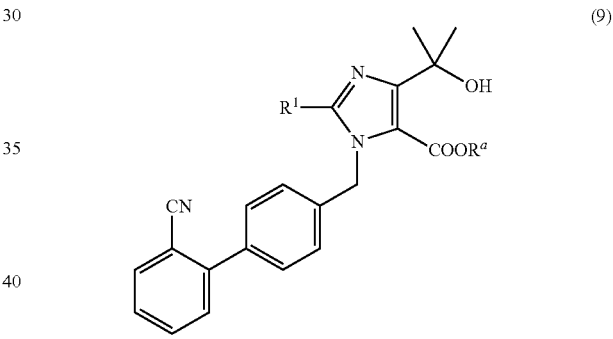

(wherein $R^1$ represents a hydrogen atom or a $C_1$-$C_4$ alkyl group, and $R^a$ represents a hydrogen atom or a $C_1$-$C_4$ alkyl group)

by reacting a compound having the formula (14):

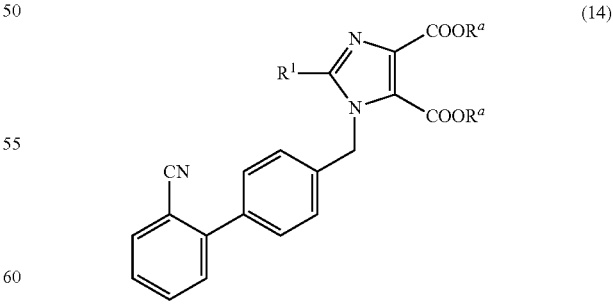

(wherein $R^1$ represents a hydrogen atom or a $C_1$-$C_4$ alkyl group, and $R^a$ represents a hydrogen atom or a $C_1$-$C_4$ alkyl group) with a compound having the formula MeMgX (wherein X represents a chloro group, a bromo group or an iodo group);

[25] The production method according to [24], wherein $R^1$ is a 1-propyl group, and $R^a$ is an ethyl group;
[26] The production method according to [24] or [25], wherein X is a chloro group;
[27] The production method according to [24], wherein $R^1$ is a 1-propyl group, $R^a$ is an ethyl group and X is a chloro group;
[28] A method for producing a compound having the formula (13a):

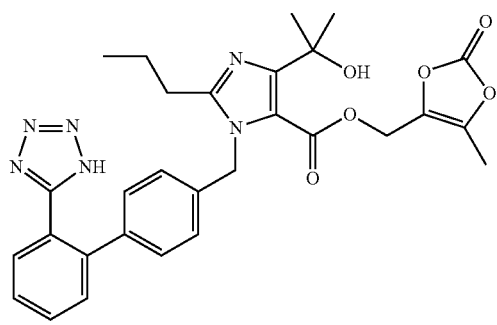

a part of the reaction steps of which comprises the production method according to any one of [1] to [12];
[29] A method for producing a compound having the formula (13a):

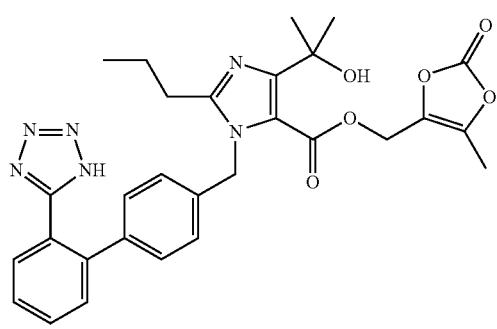

a part of the reaction steps of which comprises the production method according to any one of [13] to [15];
[30] A method for producing a compound having the formula (13a):

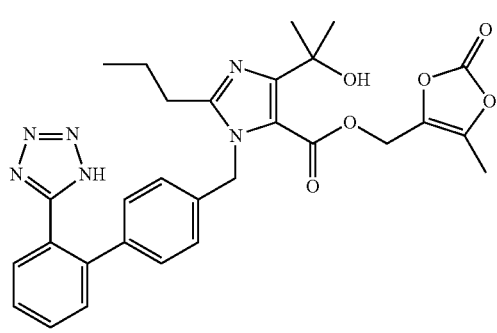

a part of the reaction steps of which comprises the production method according to any one of [16] to [23];

[31] A production method of a compound having the formula (13a):

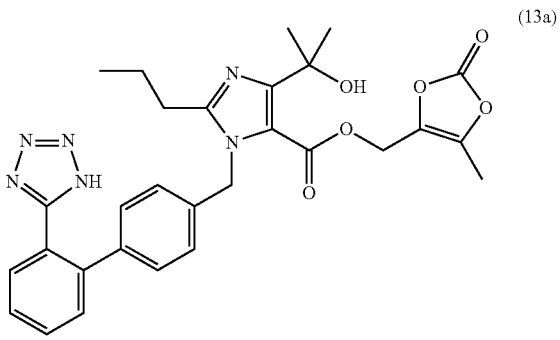 [SMILES: CCCc1nc(C(C)(C)O)c(C(=O)OCc2oc(=O)oc2C)n1Cc1ccc(-c2ccccc2-c2nnn[nH]2)cc1]

a part of the reaction steps of which comprises the production method according to any one of [24] to [27];
[32] A compound having the formula (14a):

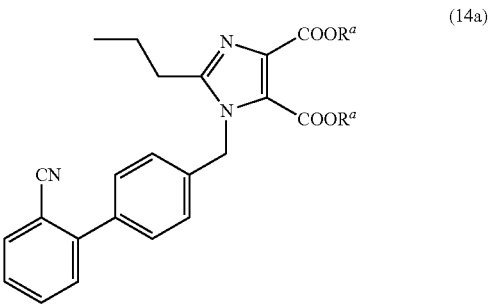

(wherein, $R^a$ represents a hydrogen atom or a $C_1$-$C_4$ alkyl group), which is a synthetic intermediate for producing the compound having the formula (13a):

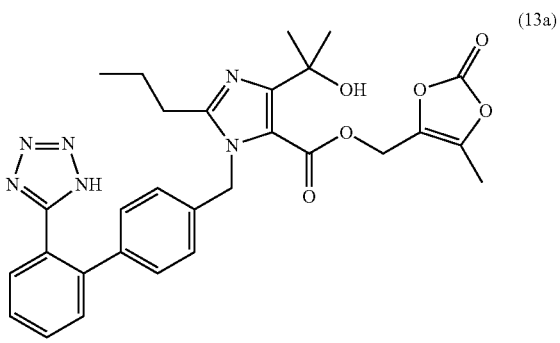 [SMILES: CCCc1nc(C(C)(C)O)c(C(=O)OCc2oc(=O)oc2C)n1Cc1ccc(-c2ccccc2-c2nnn[nH]2)cc1]

[33] The compound having the formula (14a) according to [32], wherein $R^a$ is an ethyl group.

In the present invention, each of the substituents has the meanings indicated below.

"$C_1$-$C_4$ alkyl" in the case of $R^1$ represents a straight-chain or branched-chain alkyl group having 1 to 4 carbon atoms, and may be for example methyl, ethyl, 1-propyl, 2-propyl, 1-butyl, 2-butyl or 2-methyl-2-propyl, preferably 1-propyl or 1-butyl, and most preferably 1-propyl.

"$C_1$-$C_4$ alkyl" in the case of $R^a$ represents a straight-chain or branched-chain alkyl group having 1 to 4 carbon atoms, and may be for example methyl, ethyl, 1-propyl, 2-propyl, 1-butyl, 2-butyl or 2-methyl-2-propyl, preferably methyl or ethyl, and most preferably ethyl.

$R^a$ is preferably a $C_1$-$C_4$ alkyl group.

"$C_1$-$C_6$ alkyl group" in the case of $R^b$ represents a straight-chain or branched-chain alkyl having 1 to 6 carbon atoms, and may be for example methyl, ethyl, 1-propyl, 2-propyl, 1-butyl, 2-butyl, 2-methyl-2-propyl, 1-pentyl or 1-hexyl, preferably methyl or ethyl, and most preferably methyl.

"Alkali metal" in the case of M is preferably lithium, sodium or potassium, and most preferably sodium. "Alkaline earth metal" in the case of M is preferably magnesium or calcium.

X is preferably a chloro group or a bromo group, and most preferably a chloro group.

Compounds related to the present invention can form hydrates or solvates by placing in air or mixing with water or an organic solvent. These hydrates or solvates are included in compounds related to the present invention.

In the present invention, the chemical purity of a compound or the percentage content of a compound as an impurity can be determined in accordance with known methods in the field of organic chemistry, and can be determined according to, for example, the peak area ratio as determined by high-performance liquid chromatography (hereinafter also referred to as HPLC) or weight %, and preferably according to the peak area ratio as determined by HPLC. The measurement conditions of HPLC can be suitably selected.

In the present invention, 4-(1-hydroxy-1-methylethyl)-2-propyl-1-[2'-(1H-tetrazol-5-yl)biphenyl-4-yl]methyl-1H-imidazole-5-carboxylic acid indicates compound (10a):

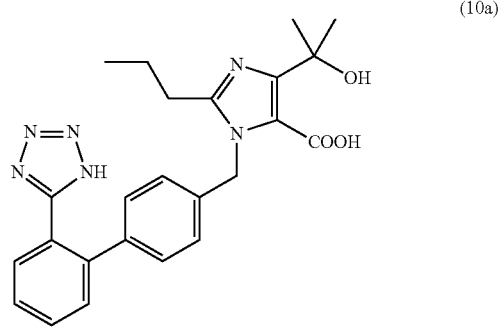 [SMILES: CCCc1nc(C(C)(C)O)c(C(=O)O)n1Cc1ccc(-c2ccccc2-c2nnn[nH]2)cc1]

(10a)

and (5-methyl-2-oxo-1,3-dioxolen-4-yl)methyl 4-(1-hydroxy-1-methylethyl)-2-propyl-1-[2'-(1H-tetrazol-5-yl)biphenyl-4-yl]methyl-1H-imidazole-5-carboxylate indicates compound (13a):

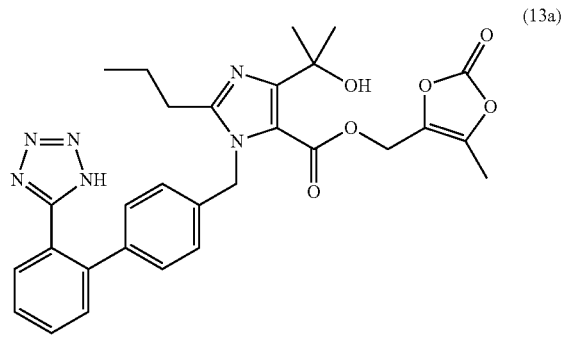 [SMILES: CCCc1nc(C(C)(C)O)c(C(=O)OCc2oc(=O)oc2C)n1Cc1ccc(-c2ccccc2-c2nnn[nH]2)cc1]

(13a)

The production method of the present invention can be carried out in accordance with the following Method A or Method B.

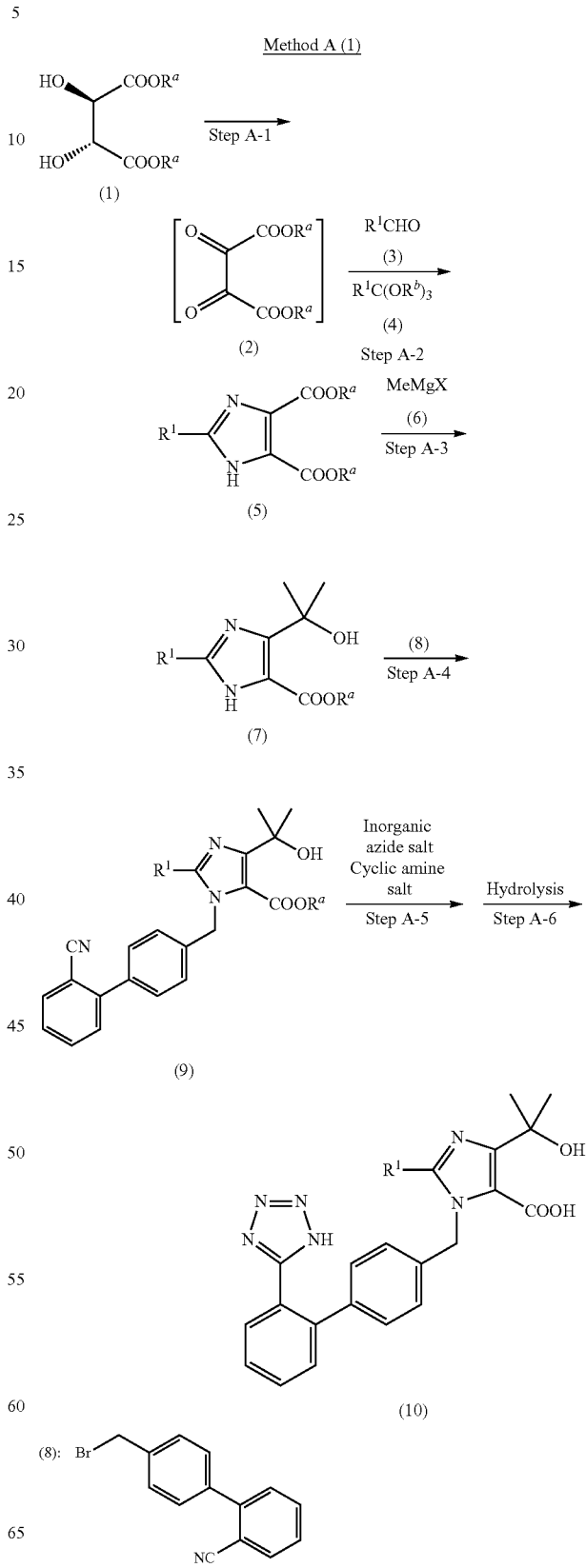

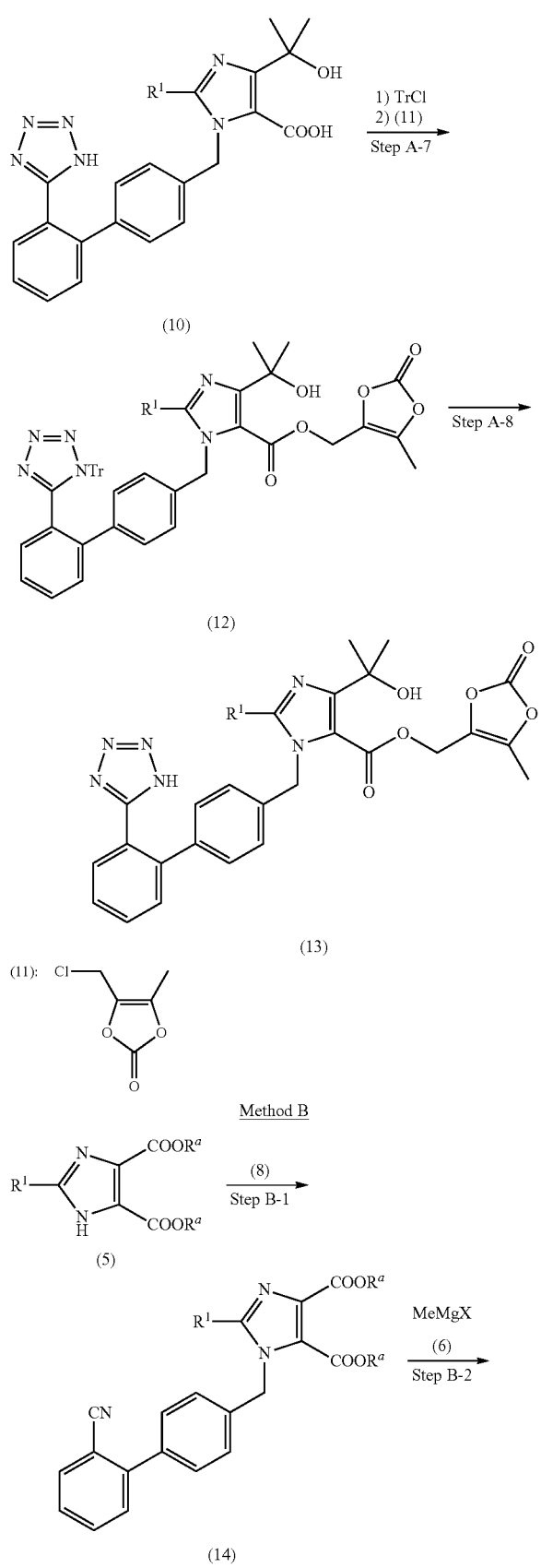

In Method A or Method B, $R^1$, $R^a$, $R^b$, M, X and Tr have the same meanings as defined above. In the present invention, a compound having the formula (1) is also referred to as Compound (1). This applies similarly to other numbered compounds.

There are no limitations on the solvent used in the reactions of each of the steps of Method A or Method B provided it does not inhibit the reaction and dissolves the starting materials to a certain degree, and the solvent is selected, for example, from the following solvent group. The solvent group consists of aliphatic hydrocarbons such as hexane, pentane, petroleum ether or cyclohexane; aromatic hydrocarbons such as benzene, toluene or xylene; isoparaffin hydrocarbons such as Isopar E (Shell), Isopar G (Shell), Isopar H (Shell), Isopar L (Shell), Isopar M (Shell), IP Clean LX (Idemitsu), IP Clean HX (Idemitsu), IP Solvent 1620 (Idemitsu), IP Solvent 2028 (Idemitsu), Marcasol R (Maruzen), Marcasol 8 (Maruzen), Isosol 300 (Nippon Petrochemical), Shellsol TG (Shell), Shellsol TK (Shell) or Shellsol TM (Shell); halogenated hydrocarbons such as methylene chloride, chloroform, carbon tetrachloride, dichloroethane, chlorobenzene or dichlorobenzene; ethers such as diethyl ether, diisopropyl ether, methyl t-butyl ether, cyclopentyl methyl ether, tetrahydrofuran, 3-methyltetrahydrofuran, dioxane, dimethoxyethane (such as 1,2-dimethoxyethane) or diethylene glycol dimethyl ether; ketones such as acetone, methyl ethyl ketone, methyl isobutyl ketone or cyclohexanone; esters such as ethyl acetate, propyl acetate or butyl acetate; nitriles such as acetonitrile, propionitrile, butyronitrile or isobutyronitrile; carboxylic acids such as acetic acid or propionic acid; alcohols such as methanol, ethanol, 1-propanol, 2-propanol, 1-butanol, 2-butanol, 2-methyl-1-propanolor 2-methyl-2-propanol; amides such as formamide, N,N-dimethylformamide, N,N-dimethylacetamide, N-methyl-2-pyrrolidone or hexamethylphosphoramide; sulfoxides such as dimethyl sulfoxide; sulfolanes such as sulfolane; water; and mixtures thereof.

In the reactions of each of the steps of Method A or Method B, the reaction temperature differs depending on the solvent, the starting material(s), the reagent(s) and the like, and is suitably selected in accordance therewith. In addition, the reaction time also differs depending on the solvent, the starting material(s), the reagent(s), the reaction temperature and the like, and is suitably selected in accordance therewith.

In the reactions of each of the steps of Method A or Method B, the desired compound of each step can be isolated from the reaction mixture in accordance with a known method after the completion of the reaction. The desired compound can be obtained by, for example, (i) filtering off an insoluble material such as a catalyst as necessary, (ii) adding water and a solvent immiscible with water (such as ethyl acetate) to the reaction mixture followed by extracting the desired compound, (iii) washing the organic layer with water as necessary and drying using a desiccant (such as anhydrous magnesium sulfate), and (iv) evaporating the solvent. In addition, the desired compound can also be obtained by adding a solvent that does not dissolve the desired compound (such as water) to the reaction mixture, adjusting the pH of the reaction mixture as necessary, and filtering out the precipitated crystals. The resulting desired compound can be further purified as necessary according to a known method (such as recrystallization, re-precipitation or silica gel column chromatography). In addition, the resulting desired compound can also be used in the next reaction without purifying.

In the reactions of each of the steps of Method A or Method B, in the case where the reaction is inhibited as a result of $R^a$ of the starting material being a hydrogen atom, the carboxy group(s) may be protected and de-protected in accordance with a known method as necessary (for example, T. W. Greene, P.G. Wuts, Protective Groups in Organic Synthesis, Third Edition, 1999, John Wiley & Sons, Inc.).

(Method A)

Method A [Method A (1) and A (2)] indicates a method for producing compound (13).

(Step A-1)

Step A-1 is a step for producing compound (2) by oxidizing known compound (1) using an oxidizing agent in the presence of a radical initiation reagent and acid. In Step A-1, an optical isomer or a racemic form of compound (1) can also be used instead of compound (1).

There are no limitations on the radical initiation reagent provided it can initiate a radical reaction, and it may be for example an azobis compound such as 2,2'-azobisisobutyronitrile, 2,2'-azobis-2-methylbutyronitrile, 2,2'-azobis-2,4-dimethylvaleronitrile, 2,2'-azobis(4-methoxy-2,4-dimethylvaleronitrile), 1,1'-azobis-1-cyclohexanecarbonitrile, dimethyl-2,2'-azobisisobutyrate, 4,4'-azobis-4-cyanovaleric acid or 1,1'-azobis(1-acetoxy-1-phenylethane); organic peroxides such as dibenzoyl peroxide, di(3-methylbenzoyl) peroxide, benzoyl(3-methylbenzoyl) peroxide, dilauroyl peroxide, diisobutyl peroxide, t-butylperoxy-2-ethylhexanoate, 1,1,3,3-tetramethylbutylperoxy-2-ethylhexanoate, t-butyl peroxypivalate or t-butyl peroxyneodecanoate; or trialkyl borane compounds such as triethyl borane or tributyl borane, preferably azobis compounds, more preferably 2,2'-azobisisobutyronitrile or 2,2'-azobis(4-methoxy-2,4-dimethylvaleronitrile), and most preferably 2,2'-azobis(4-methoxy-2,4-dimethylvaleronitrile).

The amount of the radical initiation reagent relative to compound (1) is usually a catalytic amount, preferably 0.001 to 50 mol %, more preferably 0.005 to 10 mol %, and most preferably 0.01 to 1 mol %.

The acid used may be for example an organic acid such as formic acid, acetic acid, propionic acid, butyric acid, isobutyric acid, valeric acid, isovaleric acid, pivalic acid, trifluoroacetic acid or pentafluoropropionic acid; organic sulfonic acids such as methanesulfonic acid, benzenesulfonic acid, p-toluenesulfonic acid, camphorsulfonic acid or trifluoromethanesulfonic acid; or inorganic acids such as hydrogen chloride, hydrochloric acid, hydrobromic acid, hydroiodic acid, phosphoric acid, sulfuric acid or nitric acid, preferably organic acids, and most preferably acetic acid.

There are no limitations on the oxidizing agent used provided it can be used in an oxidation reaction of a hydroxy group to an oxo group, and it may be for example a halogenosuccinimide compound such as N-chlorosuccinimide, N-bromosuccinimide or N-iodosuccinimide; a dihalogenohydantoin compound such as 1,3-dichloro-5,5-dimethylhydantoin or 1,3-dibromo-5,5-dimethylhydantoin [compound (16)]; bromine; chlorites such as sodium chlorite or potassium chlorite; bromites such as sodium bromite or potassium bromite; hypochlorites such as sodium hypochlorite or potassium hypochlorite; hypobromites such as sodium hypobromite or potassium hypobromite; manganese compounds such as potassium permanganate or manganese dioxide; or periodic acid compounds such as sodium periodate or periodic acid, preferably halogenosuccinimide compounds or dihalogenohydantoin compounds, more preferably N-bromosuccinimide or 1,3-dibromo-5,5-dimethylhydantoin, and most preferably 1,3-dibromo-5,5-dimethylhydantoin.

The solvent used is preferably an aromatic hydrocarbon, an ether, an ester or an organic acid, more preferably an ester or an organic acid, even more preferably an organic acid, and most preferably acetic acid.

The reaction temperature is preferably 0 to 100° C. and more preferably 20 to 80° C.

The reaction time is preferably 30 minutes to 12 hours and more preferably 1 to 6 hours.

Steps A-1 and A-2 can be carried out under light-shielding or non-light-shielding conditions, preferably under light-shielding conditions. Light-shielding conditions include complete light-shielding which means a condition where no light whatsoever shines onto the reaction solution, and substantial light-shielding which means a condition where light hardly shines onto the reaction solution, and is preferably substantial light-shielding.

Step A-2 is preferably carried out in continuation from Step A-1 without isolating compound (2) obtained in Step A-1.

(Step A-2)

Step A-2 is a step for producing compound (5) by reacting compound (2) with an ammonia-generating reagent and compound (3) or compound (4).

The ammonia-generating reagent used may be for example an ammonium salt such as ammonium acetate, ammonium propionate, ammonium isobutyrate, ammonium pivalate or ammonium carbonate; or aqueous ammonia, preferably an ammonium salt and most preferably ammonium acetate.

Compound (3) used is preferably formaldehyde, acetaldehyde, propanal, 1-butanal or 1-pentanal, and most preferably 1-butanal. Compound (4) used is preferably an orthoformic acid ester such as methyl orthoformate or ethyl orthoformate; an orthoacetic acid ester such as methyl orthoacetate or ethyl orthoacetate; an orthopropionic acid ester such as methyl orthopropionate or ethyl orthopropionate; an orthobutanoic acid ester such as methyl orthobutanoate or ethyl orthobutanoate; or an orthopentanoic acid ester such as methyl orthopentanoate, more preferably an orthobutanoic acid ester, and most preferably methyl orthobutanoate. Compound (3) is preferably used in Step A-2.

The solvent used is preferably an ether, a nitrile or an alcohol, more preferably an ether, even more preferably tetrahydrofuran, dioxane or 1,2-dimethoxyethane, and most preferably tetrahydrofuran or 1,2-dimethoxyethane.

The reaction temperature is preferably 0 to 100° C. and more preferably 20 to 80° C.

The reaction time is preferably 30 minutes to 48 hours and more preferably 1 to 6 hours.

Compound (5) can also be obtained as a salt by combining with an acid. There are no limitations on the acid which can form a salt with compound (5) provided it can form a salt with an amine, and it may be for example the acids indicated in Step A-5, preferably organic acids or inorganic acids, more preferably acetic acid, trifluoroacetic acid, hydrochloric acid, hydrobromic acid or sulfuric acid, more preferably hydrochloric acid or hydrobromic acid, and most preferably hydrochloric acid.

A salt of compound (5) can be converted to compound (5) by removing the acid by treating with a base. The bases used may be for example alkali metal carbonates, alkali metal hydroxides or alkaline earth metal hydroxides indicated in Step A-4, preferably alkaline metal hydroxides and most preferably sodium hydroxide or potassium hydroxide.

(Step A-3)

Step A-3 is a step for producing compound (7) by reacting compound (5) with compound (6).

Compound (6) used is preferably methyl magnesium chloride or methyl magnesium bromide, and most preferably methyl magnesium chloride.

The solvent used is preferably an aliphatic hydrocarbon, an aromatic hydrocarbon, an ether or a mixture thereof, more preferably toluene, cyclopentyl methyl ether, tetrahydrofuran or a mixture thereof, and most preferably a mixture of toluene and tetrahydrofuran.

The reaction temperature is preferably −40 to 100° C. and more preferably −20 to 20° C.

The reaction time is preferably 30 minutes to 12 hours and more preferably 1 to 6 hours.

(Step A-4)

Step A-4 is a step for producing compound (9) by reacting compound (7) with compound (8) in the presence of a base.

There are no limitations on the base used provided it can be used in an alkylation reaction of a nitrogen atom, and it may be for example an alkali metal carbonate such as lithium carbonate, sodium carbonate, potassium carbonate or cesium carbonate; an alkali metal hydrogencarbonate such as lithium hydrogencarbonate, sodium hydrogencarbonate or potassium hydrogencarbonate; an alkali metal hydroxide such as lithium hydroxide, sodium hydroxide or potassium hydroxide; an alkaline earth metal hydroxide such as calcium hydroxide or barium hydroxide; an alkali metal hydride such as lithium hydride, sodium hydride or potassium hydride; an alkali metal amide such as lithium amide, sodium amide or potassium amide; an alkali metal alkoxide such as lithium methoxide, sodium methoxide, sodium ethoxide, sodium tert-butoxide or potassium tert-butoxide; a lithium alkyl amide such as lithium diisopropyl amide, a lithium silyl amide such as lithium bistrimethylsilyl amide or sodium bistrimethylsilyl amide; or an organic amine such as triethylamine, tributylamine, N,N-diisopropylethylamine, N-methylpiperidine, N-methylmorpholine, N-ethylmorpholine, pyridine, picoline, 4-dimethylaminopyridine, 4-pyrrolidinopyridine, 2,6-di(tert-butyl)-4-methylpyridine, quinoline, N,N-dimethylaniline, N,N-diethylaniline, 1,5-diazabicyclo[4.3.0]non-5-ene (DBN), 1,4-diazabicyclo[2.2.2]octane (DABCO) or 1,8-diazabicyclo[5.4.0]undec-7-ene (DBU), preferably an alkali metal carbonate, an alkali metal hydride, an alkali metal alkoxide or a lithium silyl amide, more preferably an alkali metal carbonate or an alkali metal alkoxide, even more preferably sodium carbonate, potassium carbonate, sodium methoxide or sodium ethoxide, and most preferably sodium methoxide or sodium ethoxide.

The solvent used is preferably an aromatic hydrocarbon, an ether, a ketone, an amide or a mixture thereof, more preferably toluene, acetone, dimethylformamide, dimethylacetamide or a mixture thereof, and most preferably a mixture of toluene and dimethylformamide.

The reaction temperature is preferably −20 to 100° C. and more preferably 0 to 80° C.

The reaction time is preferably 30 minutes to 12 hours and more preferably 1 to 6 hours.

(Step A-5)

Step A-5 is a step for reacting compound (9) with an inorganic azide salt in the presence of a cyclic amine salt.

The cyclic amine salt used indicates a salt formed by a cyclic amine and an acid.

The cyclic amine that forms the cyclic amine salt indicates a saturated heterocyclic group which contains one or more nitrogen atoms in the ring and may contain one or more atoms selected from the group consisting of an oxygen atom and a sulfur atom, and it may be for example aziridine, N-methylaziridine, azetidine, N-methylazetidine, pyrrolidine, N-methylpyrrolidine, piperidine, N-methylpiperidine, N-ethylpiperidine, piperazine, N,N-dimethylpiperazine, N,N-diethylpiperazine, morpholine, N-methylmorpholine, N-ethylmorpholine, thiomorpholine, N-methylthiomorpholine, N-ethylthiomorpholine, homopiperidine, N-methylhomopiperidine, homopiperazine or N,N-dimethylhomopiperazine, preferably N-methylpyrrolidine, N-methylpiperidine, N,N-dimethylpiperazine, N-methylmorpholine, N-methylthiomorpholine, N-methylhomopiperidine or N,N-dimethylhomopiperazine, more preferably N-methylpiperidine, N,N-dimethylpiperazine, N-methylmorpholine or N-methylthiomorpholine, and most preferably N-methylpiperidine, N,N-dimethylpiperazine or N-methylmorpholine. In addition, from a different viewpoint, the cyclic amine is preferably N-methylpyrrolidine, N-methylpiperidine, N,N-dimethylpiperazine, N-methylthiomorpholine, N-methylhomopiperidine or N,N-dimethylhomopiperazine, more preferably N-methylpiperidine, N,N-dimethylpiperazine or N-methylthiomorpholine, and most preferably N-methylpiperidine or N,N-dimethylpiperazine.

There are no limitations on the acid that forms a cyclic amine salt provided it can form a salt with an amine, and it may be for example an organic acid such as formic acid, acetic acid, propionic acid, trifluoroacetic acid, pentafluoropropionic acid or oxalic acid; an organic sulfonic acid such as methanesulfonic acid, benzenesulfonic acid, p-toluenesulfonic acid, camphorsulfonic acid or trifluoromethanesulfonic acid; or an inorganic acid such as hydrogen chloride, hydrochloric acid, hydrobromic acid, hydroiodic acid, phosphoric acid, sulfuric acid, nitric acid, boric acid, carbonic acid, hydrogen sulfide or hydrogen azide, preferably an organic acid or an inorganic acid, more preferably acetic acid, trifluoroacetic acid, hydrochloric acid, hydrobromic acid, sulfuric acid or hydrogen azide, even more preferably hydrochloric acid, hydrobromic acid or sulfuric acid, still more preferably hydrochloric acid or hydrobromic acid, and most preferably hydrochloric acid.

The cyclic amine salt is preferably a hydrochloride or a hydrobromide of N-methylpyrrolidine, N-methylpiperidine, N,N-dimethylpiperazine, N-methylmorpholine, N-methylthiomorpholine, N-methylhomopiperidine or N,N-dimethylhomopiperazine, more preferably a hydrochloride or a hydrobromide of N-methylpiperidine, N,N-dimethylpiperazine, N-methylmorpholine or N-methylthiomorpholine, even more preferably a hydrochloride or a hydrobromide of N-methylpiperidine, N,N-dimethylpiperazine or N-methylmorpholine, still more preferably a N-methylpiperidine hydrochloride, N,N-dimethylpiperazine dihydrochloride or N-methylmorpholine hydrochloride, and most preferably N-methylpiperidine hydrochloride or N,N-dimethylpiperazine dihydrochloride. In the present invention, hydrochlorides include monohydrochlorides and dihydrochlorides, and hydrobromides include monohydrobromides and dihydrobromides. In Step A-5, a commercially available cyclic amine salt can also be used, and the cyclic amine salt can also be formed from a cyclic amine and an acid in the reaction solution.

The amount (molar ratio) of the cyclic amine salt relative to compound (9) is preferably 1 to 5, more preferably 2 to 4 and even more preferably 2.5 to 3.5.

The inorganic azide salt used is preferably sodium azide.

The solvent used is preferably an aromatic hydrocarbon, ether, ketone, amide or mixture thereof, more preferably an aromatic hydrocarbon, even more preferably toluene or xylene, and most preferably toluene. In addition, from a different viewpoint, the solvent used is preferably toluene, xylene, cyclopentyl methyl ether, methyl isobutyl ketone, dimethylformamide or a mixture thereof.

The reaction temperature is preferably 0 to 200° C. and more preferably 80 to 150° C.

The reaction time is preferably 1 to 72 hours and more preferably 3 to 48 hours.

After completion of the reaction of Step A-5, excess inorganic azide salt can be decomposed with a nitrite (preferably sodium nitrite or potassium nitrite) under acidic conditions.

Step A-6 is not carried out in the case $R^a$ of compound (9) in Step A-5 is a hydrogen atom. Step A-6 is subsequently carried out in the case $R^a$ of compound (9) in Step A-5 is a $C_1$-$C_4$ alkyl group, and preferably Step A-6 is carried out following Step A-5 without isolating the compound obtained in Step A-5.

(Step A-6)

Step A-6 is a step for producing compound (10) by hydrolyzing the compound obtained in Step A-5 under basic conditions.

There are no limitations on the base used provided it can be used to hydrolyze an ester group, and it may be for example an alkali metal carbonate, an alkali metal hydroxide or an alkaline earth metal hydroxide indicated in Step A-4, preferably an alkali metal hydroxide, and most preferably sodium hydroxide or potassium hydroxide.

The solvent used is preferably an aromatic hydrocarbon, an alcohol or a mixture thereof, more preferably toluene, xylene, methanol, ethanol, 2-propanol or a mixture thereof, and most preferably a mixture of toluene and 2-propanol. The same solvent is preferably used in Steps A-5 and A-6. Water required for hydrolysis is used in Step A-6.

The reaction temperature is preferably 0 to 200° C. and more preferably 0 to 40° C.

The reaction time is preferably 1 to 72 hours and more preferably 1 to 10 hours.

After completion of the reaction, compound (10) can be obtained by adjusting the pH of the reaction mixture to an acidic pH by adding hydrochloric acid or the like to the reaction mixture, and then filtering out the precipitated crystals. The adjusted pH of the reaction mixture is preferably 1 to 5 and more preferably 2 to 4.

(Step A-7)

Step A-7 is a step for producing compound (12) by reacting compound (10) with triphenylmethyl chloride and then reacting the resulting compound with compound (11).

Step A-7 can be carried out in accordance with a known method or a method similar thereto [for example, Examples 79(a) and 78(a) of JP (Toku-Kou-Hei) 7-121918 (the corresponding: U.S. Pat. No. 5,616,599)].

(Step A-8)

Step A-8 is a step for producing compound (13) by removing a triphenylmethyl group of compound (12) in the presence of an acid.

Step A-8 can be carried out in accordance with a known method or a method similar thereto [for example, Example 78(b) of JP (Toku-Kou-Hei) 7-121918 (the corresponding: U.S. Pat. No. 5,616,599)].

(Method B)

Method B is a method for producing compound (9) used in Method A.

(Step B-1)

Step B-1 is a step for producing compound (14) by reacting compound (5) with compound (8) in the presence of a base.

Step B-1 can be carried out in accordance with a method similar to Step A-4.

(Step B-2)

Step B-2 is a step for producing compound (9) by reacting compound (14) with compound (6).

Step B-2 can be carried out in accordance with a method similar to Step A-3.

Effects of the Invention

The production method of the present invention is superior to a known production method from the industrial viewpoints of industrial practicality, total yield, reaction selectivity, providing a desired compound with high purity and the like (and particularly with respect to the points indicated below).

(i) An industrial reaction vessel such as a reactor is usually sealed, and a reaction in such a reaction vessel is carried out under light-shielding conditions. Since the reaction indicated in the known Method X does not proceed under light-shielding conditions, it does not have industrial practicality. In contrast, since the reaction in the production method of the present invention [the method for producing compound (5) from compound (1)] proceeds efficiently under light-shielding conditions, it has industrial practicality. In addition, the production method of the present invention [the method for producing compound (5) from compound (1)] is superior to the reaction indicated in the known Method X in terms of yield, even under non-light-shielding conditions.

(ii) Although a method for converting a cyano group to a tetrazolyl group in the presence of triethylamine hydrochloride is known, the corresponding method using a cyclic amine salt is not known (see Method Y: Patent reference 3). The production method of the present invention that uses a cyclic amine salt [the method for producing compound (10) from compound (9)] is superior to a known method in terms of yield.

(iii) In a reaction between a compound having a cyano group and an ester group and a nucleophilic reagent, it would be predicted that the desired compound would not be obtained in good yield due to the possibility of both groups reacting with the nucleophilic reagent. In addition, examples are also known in which the cyano group of a compound having a cyano group and an ester group selectively reacts (for example, Chemistry Letters, 1983, Vol. 8, p. 1231; Tetrahedron Letter, 2000, Vol. 41, p. 8803; Journal of Organometallic Chemistry, 1991, Vol. 403, p. 21). Moreover, although a reaction between a 1-biphenylmethyl-4-methoxycarbonylimidazole compound and a methyl Grignard reagent is known, a cyano group is not present in the starting raw materials (see Method Z: Patent reference 4). In contrast, in the reaction in the production method of the present invention [the method for producing compound (9) from compound (14)], an ester group selectively reacts, and the desired compound (9) is obtained in good yield.

DETAILED DESCRIPTION

Examples

Although the following Examples and Reference Examples provide a more detailed explanation of the present invention, the scope of the present invention is not limited thereto. In the following Examples, Isopar E (trade name) and Isopar G (trade name) are available from Shell Company.

Example 1

Diethyl Dioxobutanedioate (Step A-1)

Example 1 was carried out under light-shielding conditions.

L-Tartaric acid diethyl ester (300 g), acetic acid (3 l), 1,3-dibromo-5,5-dimethylhydantoin (894 g) and 2,2'-azobis(4-methoxy-2,4-dimethylvaleronitrile) (4.5 g) were mixed, and the reaction solution was stirred at 55° C. for 3 hours. The reaction solution was concentrated under reduced pressure until its volume became 1.5 l to afford a solution of the title compound in acetic acid as a yellow liquid.

$^1$H-NMR (400 MHz, D$_2$O) δ: 1.31 (t, J=7.0 Hz, 6H), 4.29 (q, J=7.0 Hz, 4H).

Example 2

Diethyl 2-propyl-1H-imidazole-4,5-dicarboxylate (Step A-2)

Example 2 was carried out under light-shielding conditions.

To a suspension of ammonium acetate (900 g) in tetrahydrofuran (3 l), a solution of diethyl dioxobutanedioate obtained in Example 1 in acetic acid (1.5 l) and a solution of butanal (157.4 g) in tetrahydrofuran (1.2 l) were added dropwise. The reaction solution was stirred at 60° C. for 3 hours followed by ice cooling, and 5N aqueous sodium hydroxide solution was added to separate the organic layer. After the organic layer was concentrated under reduced pressure, toluene and 1N hydrochloric acid were added to the residue to separate the aqueous layer. To the aqueous layer, sodium chloride and toluene were added followed by ice cooling, and 5N aqueous sodium hydroxide solution was added. The resulting aqueous layer was extracted with toluene, and the organic layers were combined, followed by washing with saturated aqueous sodium bicarbonate solution. The organic layer was concentrated under reduced pressure, Isopar G was added to the residue, and then it was stirred for 2 hours after crystal precipitation. Further Isopar G was added to the organic layer, followed by stirring for 2.5 hours under ice cooling. The precipitated crystals were collected by filtration, and subsequently dried under reduced pressure to afford the title compound (290 g) as yellow crystals.

$^1$H-NMR (400 MHz, CDCl$_3$) δ: 0.97 (t, J=7.4 Hz, 3H), 1.38 (t, J=7.2 Hz, 6H), 1.79 (dt, J=7.4, 7.7 Hz, 2H), 2.76 (t, J=7.7 Hz, 2H), 4.39 (q, J=7.2 Hz, 4H), 10.5 (brs, 1H).

Elemental analysis:

Calc. C, 56.68%, H, 7.13%, N, 11.02%

Obsd. C, 56.82%, H, 7.23%, N, 11.04%.

Example 3

Diethyl 2-propyl-1H-imidazole-4,5-dicarboxylate (Steps A-1 and A-2)

Example 3 was carried out under light-shielding conditions.

L-Tartaric acid diethyl ester (100.3 g), acetic acid (1 l), 1,3-dibromo-5,5-dimethylhydantoin (304 g) and 2,2'-azobis(4-methoxy-2,4-dimethylvaleronitrile) (1.5 g) were mixed, and the reaction solution was stirred at 55° C. for 3 hours. The reaction solution was concentrated under reduced pressure until its volume became 500 ml to afford a solution of diethyl dioxobutanedioate in acetic acid as a yellow liquid.

To a suspension of ammonium acetate (100 g) in tetrahydrofuran (1 l), a solution of diethyl dioxobutanedioate in an acetic acid obtained above and a solution of butanal (52.5 g) in tetrahydrofuran (500 ml) were added dropwise. The reaction solution was stirred at 60° C. for 3 hours followed by ice cooling, and 5N aqueous sodium hydroxide solution was added to separate the organic layer. After the organic layer was concentrated under reduced pressure, toluene and 1N hydrochloric acid were added to the residue to separate the aqueous layer, subsequently sodium chloride and toluene were added to the aqueous layer followed by ice cooling, and 5N aqueous sodium hydroxide solution was added. The resulting aqueous layer was extracted with toluene, and the organic layers were combined, followed by washing with saturated aqueous sodium bicarbonate solution. The organic layer was concentrated under reduced pressure, Isopar G was added to the residue, and then it was stirred for 1 hour after crystal precipitation. Further Isopar G was added to the organic layer, followed by stirring for 2.5 hours under ice cooling. The precipitated crystals were collected by filtration, and subsequently dried under reduced pressure to afford the title compound (96.6 g) as yellow crystals. Each spectral data of the obtained compound coincided with that of the compound in Example 2.

Example 4

Diethyl 2-propyl-1H-imidazole-4,5-dicarboxylate (Steps A-1 and A-2)

Example 4 was carried out under light-shielding conditions.

L-Tartaric acid diethyl ester (10.0 g), acetic acid (100 ml), N-bromosuccinimide (34.5 g) and 2,2'-azobis(4-methoxy-2,4-dimethylvaleronitrile) (0.15 g) were mixed, and the reaction solution was stirred at 55° C. for 3 hours. The reaction solution was concentrated under reduced pressure until its volume became 50 ml to afford a solution of diethyl dioxobutanedioate in acetic acid as a yellow liquid.

To a suspension of ammonium acetate (10 g) in tetrahydrofuran (100 ml), a solution of diethyl dioxobutanedioate in acetic acid obtained above and a solution of butanal (5.25 g) in tetrahydrofuran (50 ml) were added dropwise. The reaction solution was stirred at 60° C. for 3 hours followed by ice cooling, and 5N aqueous sodium hydroxide solution was added to separate the organic layer. After the organic layer was concentrated under reduced pressure, toluene and 1N hydrochloric acid were added to the residue to separate the aqueous layer, subsequently sodium chloride and toluene were added to the aqueous layer followed by ice cooling, and 5N aqueous sodium hydroxide solution was added. The resulting aqueous layer was extracted with toluene, and the organic layers were combined, followed by washing with saturated aqueous sodium bicarbonate solution. The organic layer was concentrated under reduced pressure, Isopar G was added to the residue, and then it was stirred for 1 hour after crystal precipitation. Further Isopar G was added to the organic layer, followed by stirring for 2.5 hours under ice cooling. The precipitated crystals were collected by filtration, and subsequently dried under reduced pressure to afford the title compound (9.61 g) as yellow crystals. Each spectral data of the obtained compound coincided with that of the compound in Example 2.

Example 5

Diethyl 1H-imidazole-4,5-dicarboxylate (Steps A-1 and A-2)

Example 5 was carried out under light-shielding conditions.

L-Tartaric acid diethyl ester (2.0 g), acetic acid (20 ml), 1,3-dibromo-5,5-dimethylhydantoin (6.0 g) and 2,2'-azobis (4-methoxy-2,4-dimethylvaleronitrile) (30 mg) were mixed, and the reaction solution was stirred at 55° C. for 3 hours. The reaction solution was concentrated under reduced pressure until its volume became 10 ml to afford a solution of diethyl dioxobutanedioate in acetic acid as a yellow liquid.

To the obtained solution of diethyl dioxobutanedioate in acetic acid, ethyl acetate (17 ml) and acetic acid (7 ml) were added. To the reaction solution, 36% aqueous formaldehyde solution (3.45 ml) was added under ice cooling at an internal temperature of 10° C. or below, followed by addition of ammonium acetate (17.2 g) at an internal temperature of 10° C. or below. The reaction solution was stirred at room temperature for 30 minutes, followed by stirring at 50° C. for 3 hours. To the reaction solution, 5N sodium hydroxide was added, and the aqueous layer was extracted with ethyl acetate. The organic layers were combined, and dried over magnesium sulfate. Quantitative analysis of the resulting ethyl acetate solution by HPLC showed that the title compound (1.50 g, yield: 73%) was obtained.

Condition for HPLC Analysis:
Column: SHISEIDO CAPCELL PAK CN UG120 250×4.6 mm
Mobile phase: 20 mM phosphoric acid buffer solution (pH 7)/acetonitrile=70/30
Flow rate: 1.0 ml/min
Detection wavelength: 254 nm
Column temperature 40° C.
Retention time: 4.5 min.

$^1$H-NMR (400 MHz, DMSO-$d_6$) δ: 1.26 (t, J=7.0 Hz, 6H), 4.28 (q, J=7.0 Hz, 4H), 7.90 (s, 1H), 13.53 (brs, 1H).

Example 6

Ethyl 4-(1-hydroxy-1-methylethyl)-2-propyl-1H-imidazole-5-carboxylate (Step A-3)

Under a nitrogen atmosphere, diethyl 2-propyl-1H-imidazole-4,5-dicarboxylate (9.7 g) obtained in Example 2 was dissolved in a mixture of toluene (9 ml) and tetrahydrofuran (18 ml), and to the reaction solution, a mixture of a solution of methyl magnesium chloride in tetrahydrofuran (3M, 52.4 ml) and toluene (20 ml) was added dropwise under ice cooling over 5 hours. After the reaction solution was stirred for 1.5 hours, the solution was poured into water, followed by addition of 3N hydrochloric acid to the reaction mixture to adjust the pH of the reaction mixture to 7, the organic layer was washed with aqueous sodium chloride solution (10 wt %), and subsequently the aqueous layer was extracted with toluene. The organic layers were combined, and the solvent was evaporated under reduced pressure to afford the title compound (8.09 g) as a brown oil.

$^1$H-NMR (400 MHz, CDCl$_3$) δ: 0.94 (t, J=7.4 Hz, 3H), 1.31 (t, J=7.2 Hz, 6H), 1.62 (s, 6H), 1.72 (dt, J=7.4, 7.8 Hz, 2H), 2.66 (t, J=7.8 Hz, 2H), 4.34 (q, J=7.2 Hz, 2H), 6.04 (brs, 1H).

Example 7

Ethyl 1-(2'-cyanobiphenyl-4-yl)methyl-4-(1-hydroxy-1-methylethyl)-2-propyl-1H-imidazole-5-carboxylate (Step A-4)

Ethyl 4-(1-hydroxy-1-methylethyl)-2-propyl-1H-imidazole-5-carboxylate (8.09 g) obtained in Example 6 was dissolved in a mixture of toluene (28.3 ml) and N,N-dimethylacetamide (18 ml) under a nitrogen atmosphere, and to the reaction solution, sodium ethoxide (2.43 g) was added. After the reaction solution was stirred at room temperature for 1 hour, 4'-(bromomethyl)biphenyl-2-carbonitrile (9.70 g) was added, and the reaction solution was stirred at 40° C. for 4 hours. After the reaction solution was cooled to room temperature, it was poured into aqueous sodium chloride solution (5.4 wt %), and the aqueous layer was extracted with toluene. The organic layers were combined and concentrated under reduced pressure to approximately half the volume, subsequently Isopar E was added, then the mixture was stirred at room temperature for 16 hours, followed by further stirring for 1 hour under ice cooling. The precipitated crystals were collected by filtration, and subsequently dried under reduced pressure to afford the title compound (13.1 g) as white crystals.

$^1$H-NMR (400 MHz, CDCl$_3$) δ: 0.97 (t, J=7.4 Hz, 3H), 1.16 (t, J=7.2 Hz, 3H), 1.65 (s, 6H), 1.74 (dt, J=7.4, 7.8 Hz, 2H), 2.66 (t, J=7.8 Hz, 2H), 4.23 (q, J=7.2 Hz, 2H), 5.52 (s, 1H), 5.81 (s, 1H), 7.05 (d, J=8.8 Hz, 2H), 7.42-7.54 (m, 4H), 7.65 (dt, J=1.6, 7.8 Hz, 1H), 7.77 (dd, J=1.2, 8.0 Hz, 1H).

Elemental analysis:
Calc. C, 72.37%, H, 6.77%, N, 9.74%
Obsd. C, 72.41%, H, 6.81%, N, 9.69%.

Example 8

4-(1-Hydroxy-1-methylethyl)-2-propyl-1-[2'-(1H-tetrazol-5-yl)biphenyl-4-yl]methyl-1H-imidazol-5-carboxylic acid (Steps A-5 and A-6)

Example 8a

To a solution of ethyl 1-(2'-cyanobiphenyl-4-yl)methyl-4-(1-hydroxy-1-methylethyl)-2-propyl-1H-imidazol-5-carboxylate (2.0 g) obtained in Example 7 in toluene (3 ml), sodium azide (0.9 g) and N,N'-dimethylpiperazine dihydrochloride (1.3 g) were added, and the reaction solution was stirred at 96 to 100° C. for 24 hours. The reaction solution was cooled to 40° C. or below, followed by addition of toluene and 2-propanol. The reaction solution was poured into aqueous sodium nitrite solution (14.6 wt %), followed by addition of hydrochloric acid (20 wt %) to the reaction mixture to adjust the pH of the reaction mixture to 3.8. Toluene was added to the reaction mixture to separate the organic layer, followed by washing with aqueous sodium chloride solution (10 wt %). To the organic layer, aqueous sodium hydroxide solution (5 wt %) was added, and the reaction mixture was stirred for 2 hours under ice cooling. After acetonitrile was added to the separated aqueous layer, hydrochloric acid (20 wt %) was added to adjust the pH of the reaction mixture to 3.8. The precipitated crystals were collected by filtration and dried to afford the title compound (1.94 g) as white crystals.

$^1$H-NMR (400 MHz, DMSO-$d_6$) δ: 0.85 (t, J=7.3 Hz, 3H), 1.53 (tq, J=7.3, 7.6 Hz, 2H), 1.53 (s, 6H), 2.57 (t, J=7.6 Hz, 2H), 5.64 (s, 2H), 6.94 (d, J=8.3 Hz, 2H), 7.06 (d, J=8.3 Hz, 2H), 7.51-7.59 (m, 2H), 7.62-7.70 (m, 2H).

Example 8a can also be carried out using the following solvents instead of toluene. Solvents used and reaction yields are shown in Table 1.

TABLE 1

| Example | Solvent | Yield (%) |
|---|---|---|
| 8a | toluene | 89 |
| 8b | xylene | 90 |
| 8c | cyclopentyl methyl ether | 91 |
| 8d | methyl isobutyl ketone | 90 |
| 8e | toluene/N,N-dimethylformamide [9/1 (v/v)] | 91 |

Example 8a can also be carried out using the following cyclic amine salts instead of N,N'-dimethylpiperazine dihydrochloride. The molar ratio of cyclic amine salt used to ethyl 1-(2'-cyanobiphenyl-4-yl)methyl-4-(1-hydroxy-1-methylethyl)-2-propyl-1H-imidazole-5-carboxylate is 3. Cyclic amine salts used and reaction yields are shown in Table 2. As a comparison, the reaction yield in the case of using triethylamine hydrochloride which is a non-cyclic amine salt (Example 2 of Japanese Patent No. 3521304) is also shown.

TABLE 2

| Example | Cyclic amine salt | Yield (%) |
|---|---|---|
| 8a | N,N-dimethylpiperazine dihydrochloride | 89 |
| 8f | N-methylpiperidine hydrochloride | 89 |
| 8g | N-methylmorpholine hydrochloride | 90 |
| 8h | N-methylpyrrolidine hydrochloride | 87 |
|  | triethylamine hydrochloride | 72 |

From the results of Table 2, it was shown that the production method of the present invention [the method for producing compound (10) from compound (9)] was superior to the reaction indicated in the known Method Y in terms of yield.

Example 9

Diethyl 1-(2'-cyanobiphenyl-4-yl)methyl-2-propyl-1H-imidazole-4,5-dicarboxylate (Step B-1)

Diethyl 2-propyl-1H-imidazole-4,5-dicarboxylate (30.7 g) obtained in Example 2 and 4'-(bromomethyl)biphenyl-2-carbonitrile (33.4 g) were dissolved in a mixture of acetone (45 ml) and N,N-dimethylacetamide (45 ml), followed by addition of potassium carbonate (29.3 g) to the reaction solution, and the reaction solution was stirred at 55° C. for 2 hours. The reaction solution was cooled to room temperature, followed by addition of water and toluene, and the organic layer was washed with water. The solvent was evaporated under reduced pressure to afford the title compound (53.8 g) as yellow crystals.

$^1$H-NMR (400 MHz, CDCl$_3$) δ: 0.96 (t, J=7.4 Hz, 3H), 1.25 (t, J=7.2 Hz, 3H), 1.39 (t, J=7.0 Hz, 3H), 1.75 (dt, J=7.4, 7.8 Hz, 2H), 2.69 (t, J=7.8 Hz, 2H), 4.27 (q, J=7.2 Hz, 2H), 4.40 (q, J=7.0 Hz, 2H), 5.48 (s, 2H), 7.13 (d, J=8.4 Hz, 2H), 7.42-7.54 (m, 4H), 7.65 (dt, J=1.2, 7.6 Hz, 1H), 7.76 (dd, J=1.2, 7.6 Hz, 1H).

Elemental analysis:
Calc. C, 70.09%, H, 6.11%, N, 9.43%
Obsd. C, 70.28%, H, 6.13%, N, 9.48%.

Example 10

Ethyl 1-(2'-cyanobiphenyl-4-yl)methyl-4-(1-hydroxy-1-methylethyl)-2-propyl-1H-imidazol-5-carboxylate (Step B-2)

A solution of methyl magnesium chloride in tetrahydrofuran (3.0M, 9.05 ml) and a solution of diethyl 1-(2'-cyanobiphenyl-4-yl)methyl-2-propyl-1H-imidazole-4,5-dicarboxylate (5.5 g) obtained in Example 9 in toluene (16.5 ml) were simultaneously added dropwise to toluene (38.5 ml) under a nitrogen atmosphere and under ice cooling over 3 hours. The reaction solution was stirred for 30 minutes, subsequently poured into water, and 2N hydrochloric acid was added to the reaction mixture to adjust the pH of the reaction mixture to 2.2. The organic layer was washed with water, concentrated under reduced pressure to approximately half the volume, subsequently Isopar E was added, and the mixture was stirred at room temperature for 16 hours, followed by further stirring for 1 hour under ice cooling. The precipitated crystals were collected by filtration, and subsequently dried under reduced pressure to afford the title compound (4.9 g) as white crystals. Each spectral data of the obtained compound coincided with that of the compound in Example 7.

From the results of Example 10, it was shown that in the reaction in the production method of the present invention [the method for producing compound (9) from compound (14)], an ester group selectively reacts and the desired compound is obtained in good yield.

Example 11

Diethyl 2-propyl-1H-imidazole-4,5-dicarboxylate (Steps A-1 and A-2)

Example 11a

Diethyl 2-propyl-1H-imidazole-4,5-dicarboxylate hydrochloride

Example 11a was carried out under light-shielding conditions.

L-Tartaric acid diethyl ester (50.0 g), acetic acid (900 ml), 1,3-dibromo-5,5-dimethylhydantoin (149.1 g) and 2,2'-azobis(4-methoxy-2,4-dimethylvaleronitrile) (750 mg) were mixed, and the reaction solution was stirred at 70° C. for 2 hours, followed by stirring at room temperature for 16 hours. The reaction solution was concentrated under reduced pressure until its volume became approximately 300 ml to obtain a solution of diethyl dioxobutanedioate in acetic acid as a yellow liquid.

To a solution of diethyl dioxobutanedioate in acetic acid, a solution of butanal (26.2 g) in 1,2-dimethoxyethane (200 ml) was added. The resulting solution was added dropwise to a suspension of ammonium acetate (150 g) in 1,2-dimethoxyethane (550 ml). The reaction solution was stirred at room temperature for 1 hour, followed by stirring at 60° C. for 1 hour, and subsequently the solvent was evaporated under reduced pressure. Toluene was added to the residue, and 8N aqueous sodium hydroxide solution was added to separate the organic layer. After the organic layer was concentrated under reduced pressure, toluene and 1N aqueous ammonium carbonate solution were added to the residue to separate the aqueous layer. Isopropanol and concentrated hydrochloric acid were added to the organic layer and the mixture was concentrated under reduced pressure, subsequently toluene and isopropanol were further added to the residue, and then it was stirred for 1 hour after crystal precipitation. The precipitated crystals were collected by filtration, and subsequently dried under reduced pressure to afford the title compound (51.0 g) as white crystals.

$^1$H-NMR (400 MHz, CD$_3$OD) δ: 1.03 (t, J=7.3 Hz, 3H), 1.42 (t, J=7.3 Hz, 6H), 1.84 (dt, J=7.3, 7.6 Hz, 2H), 2.98 (t, J=7.6 Hz, 2H), 4.47 (q, J=7.3 Hz, 4H), 4.97 (brs, 2H).

Elemental analysis:
Calc. C, 49.57%, H, 6.59%, N, 9.64%
Obsd. C, 49.35%, H, 6.53%, N, 9.73%.

Example 11b

Diethyl 2-propyl-1H-imidazole-4,5-dicarboxylate

Diethyl 2-propyl-1H-imidazol-4,5-dicarboxylate hydrochloride (50.0 g) obtained in Example 11a and sodium chloride (50.0 g) were dissolved in water (500 ml), and 5N aqueous sodium hydroxide solution (30 ml) was added to this solution, followed by stirring for 1 hour under ice cooling. The precipitated crystals were collected by filtration, and subsequently dried under reduced pressure to afford the title compound (40.7 g) as white crystals. Each spectral data of the obtained compound coincided with that of the compound in Example 2.

Reference Example 1

Diethyl 2-propyl-1H-imidazol-4,5-dicarboxylate

Reference Example 1 was carried out under light-shielding conditions.

To a solution of L-tartaric acid diethyl ester (2.0 g) in acetic acid (20 ml), 1,3-dibromo-5,5-dimethylhydantoin (6.0 g) was added, and the reaction solution was stirred at 55° C. for 3 hours. The reaction solution was concentrated under reduced pressure until its volume became 10 ml. To a suspension of ammonium acetate (6.0 g) in tetrahydrofuran (20 ml), the acetic acid solution (10 ml) obtained above and a solution of butanal (1.04 g) in tetrahydrofuran (12 ml) were added dropwise, and the reaction solution was stirred at 60° C. for 3 hours. The reaction solution was analyzed by HPLC to show that the title compound was not produced.

Condition for HPLC analysis:
Column: SHISEIDO CAPCELL PAK CN UG120 250×4.6 mm
Mobile phase: 20 mM aqueous ammonium acetate solution/acetonitrile=65/35
Flow rate: 1.0 ml/min
Detection wavelength: 210 nm
Column temperature 40° C.
Retention time: 5.8 min.

From the results of Reference Example 1 and Examples 1 to 4, it was shown that a reaction indicated in the known Method X does not proceed under light-shielding conditions, whereas the reaction in the production method of the present invention [the method for producing compound (5) from compound (1)] efficiently proceeds under light-shielding conditions.

Reference Example 2

Diethyl 1H-imidazole-4,5-dicarboxylate

Reference Example 2 was carried out under light-shielding conditions.

To a solution of L-tartaric acid diethyl ester (2.0 g) in ethyl acetate (34.2 ml), 1,3-dibromo-5,5-dimethylhydantoin (3.3 g) was added, and the reaction solution was stirred at room temperature for 3 hours. To the reaction solution, acetic acid (17 ml) was added, and subsequently 36% aqueous formaldehyde solution (3.45 ml) was added under ice cooling at the internal temperature of 10° C. or below, followed by addition of ammonium acetate (17.2 g) at an internal temperature of 10° C. or below. The reaction solution was stirred at room temperature for 30 minutes, followed by stirring at 50° C. for 3 hours. To the reaction solution, 5N sodium hydroxide was added, and the aqueous layer was extracted with ethyl acetate. The organic layers were combined, and dried over magnesium sulfate. Quantitative analysis of the resulting ethyl acetate solution by HPLC showed that the title compound was not produced. The condition for HPLC analysis was identical with that for Example 5.

From the results of Reference Example 2 and Example 5, it was shown that a reaction indicated in the known Method X does not proceed under light-shielding conditions, whereas the reaction in the production method of the present invention [the method for producing compound (5) from compound (1)] efficiently proceeds under light-shielding conditions.

Reference Example 3

Diethyl 1H-imidazole-4,5-dicarboxylate

Reference Example 3 was carried out under non-light-shielding conditions.

To a solution of L-tartaric acid diethyl ester (2.0 g) in ethyl acetate (34.2 ml), 1,3-dibromo-5,5-dimethylhydantoin (3.3 g) was added, and the reaction solution was stirred at room temperature for 3 hours. To the reaction solution, acetic acid (17 ml) was added, and subsequently 36% aqueous formaldehyde solution (3.45 ml) was added under ice cooling at an internal temperature of 10° C. or below, followed by addition of ammonium acetate (17.2 g) at an internal temperature of 10° C. or below. The reaction solution was stirred at room temperature for 30 minutes, followed by stirring at 50° C. for 3 hours. To the reaction solution, 5N sodium hydroxide was added, and the aqueous layer was extracted with ethyl acetate. The organic layers were combined, and dried over magnesium sulfate. Quantitative analysis of the resulting ethyl acetate solution by HPLC showed that the title compound (1.24 g, yield: 60%) was obtained.

Condition for HPLC analysis is identical with that for Example 5.

From the results of Reference Example 3 and Example 5, it was shown that the production method of the present invention [the method for producing compound (5) from compound (1)] was superior to the reaction indicated in the known Method X in terms of yield even under non-light-shielding conditions.

Reference Example 4

Ethyl 4-(1-hydroxy-1-methylethyl)-2-propyl-1-[2'-(1H-tetrazol-5-yl)biphenyl-4-yl]methyl-1H-imidazole-5-carboxylate A solution of diethyl 2-propyl-1-[2'-(1H-tetrazol-5-yl)biphenyl-4-yl]methyl-1H-imidazole-4,5-dicarboxylate (0.5 g)

in tetrahydrofuran (5.0 ml) was added dropwise to a solution of methyl magnesium chloride in tetrahydrofuran (3.0M, 1.4 ml) under nitrogen atmosphere and under ice cooling over 2 hours. The reaction solution was stirred at room temperature for 3 hours, followed by addition of 1N hydrochloric acid, and the aqueous layer was extracted with ethyl acetate. The organic layers were combined, and dried over magnesium sulfate. Quantitative analysis of the resulting ethyl acetate solution by HPLC showed that the title compound (420.1 mg, yield: 85%) was obtained.

Condition for HPLC analysis:

Column: WATERS XTERRA RP18 150×4.6 mm

Mobile phase: 20 mM phosphoric acid buffer (pH 3)/acetonitrile=60/40

Flow rate: 1.0 ml/min

Detection wavelength: 254 nm

Column temperature 40° C.

Retention time: 4.9 min.

$^1$H-NMR (400 MHz, CDCl$_3$) δ: 0.90 (t, J=7.2 Hz, 3H), 1.11 (t, J=7.0 Hz, 3H), 1.44 (s, 6H), 1.66 (m, 2H), 2.37 (t, J=7.2 Hz, 2H), 4.17 (q, J=7.1 Hz, 2H), 5.38 (s, 2H), 6.76 (d, J=7.6 Hz, 2H), 7.08 (d, J=7.6 Hz, 2H), 7.41 (t, J=7.6 Hz, 4H), 7.51 (t, J=7.2 Hz, 1H), 7.58 (t, J=7.4 Hz, 1H), 7.82 (d, J=6.8 Hz, 1H).

Reference Example 5

Reactions were carried out in accordance with a method similar to Example 8a using the following solvents instead of toluene. Solvents used and reaction yields are shown in Table 3.

TABLE 3

| Reference Example | Solvent | Yield (%) |
|---|---|---|
| 5a | N,N-dimethylformamide | 73 |
| 5b | N,N-dimethylacetamide | 39 |
| 5c | 1,3-dimethyl-2-imidazolidinone | 51 |

INDUSTRIAL APPLICABILITY

The production method of the present invention is superior to known production methods from the industrial viewpoints of industrial practicality, total yield, reaction selectivity, providing a desired compound with high purity and the like.

The invention claimed is:

1. A method for producing a compound having the following formula (5):

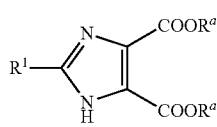

(5)

(wherein R$^1$ represents a hydrogen atom or a C$_1$-C$_4$ alkyl group, and R$^a$ represents a hydrogen atom or a C$_1$-C$_4$ alkyl group)

by oxidizing a compound having the following formula (1):

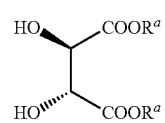

(1)

(wherein R$^a$ represents a hydrogen atom or a C$_1$-C$_4$ alkyl group) using an oxidizing agent in the presence of a radical initiation reagent, and then reacting the resulting compound with an ammonia-generating reagent and a compound having the formula R$^1$CHO (wherein R$^1$ represents a hydrogen atom or a C$_1$-C$_4$ alkyl group) or a compound having the formula R$^1$C(OR$^b$)$_3$ (wherein R$^1$ represents a hydrogen atom or a C$_1$-C$_4$ alkyl group, and R$^b$ represents a C$_1$-C$_6$ alkyl group).

2. The production method according to claim 1, wherein R$^1$ is a 1-propyl group and the compound having the formula R$^1$CHO is used.

3. The production method according to claim 1, wherein R$^a$ is an ethyl group.

4. The production method according to claim 1, wherein the radical initiation reagent is an azobis compound.

5. The production method according to claim 1, wherein the radical initiation reagent is 2,2'-azobis(4-methoxy-2,4-dimethylvaleronitrile).

6. The production method according to claim 1, wherein the oxidizing agent is a halogenosuccinimide compound or a dihalogenohydantoin compound.

7. The production method according to claim 1, wherein the oxidizing agent is 1,3-dibromo-5,5-dimethylhydantoin.

8. The production method according to claim 1, wherein the ammonia-generating reagent is an ammonium salt.

9. The production method according to claim 1, wherein the ammonia-generating reagent is ammonium acetate.

10. The production method according to claim 1, wherein the reaction is carried out under light-shielding conditions.

11. The production method according to claim 1, wherein R$^1$ is a 1-propyl group, R$^a$ is an ethyl group, the radical initiation reagent is an azobis compound, the oxidizing agent is a halogenosuccinimide compound or a dihalogenohydantoin compound, the ammonia-generating reagent is an ammonium salt, and the compound having the formula R$^1$CHO is used.

12. The production method according to claim 1, wherein R$^1$ is a 1-propyl group, R$^a$ is an ethyl group, the radical initiation reagent is 2,2'-azobis(4-methoxy-2,4-dimethylvaleronitrile), the oxidizing agent is 1,3-dibromo-5,5-dimethylhydantoin, the ammonia-generating reagent is ammonium acetate, the compound having the formula R$^1$CHO is used, and the reaction is carried out under light-shielding conditions.

13. A method for producing a compound having the formula (2):

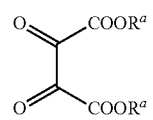

(2)

(wherein $R^a$ represents a hydrogen atom or a $C_1$-$C_4$ alkyl group) by oxidizing a compound having the formula (1):

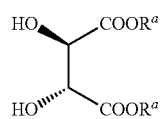
(1)

(wherein $R^a$ represents a hydrogen atom or a $C_1$-$C_4$ alkyl group) using an oxidizing agent in the presence of a radical initiation reagent.

14. The production method according to claim 13, wherein $R^a$ is an ethyl group, the radical initiation reagent is an azobis compound, and the oxidizing agent is a halogenosuccinimide compound or a dihalogenohydantoin compound.

15. The production method according to claim 13, wherein $R^a$ is an ethyl group, the radical initiation reagent is 2,2'-azobis(4-methoxy-2,4-dimethylvaleronitrile), the oxidizing agent is 1,3-dibromo-5,5-dimethylhydantoin, and the reaction is carried out under light-shielding conditions.

16. A method for producing a compound having the formula (10a):

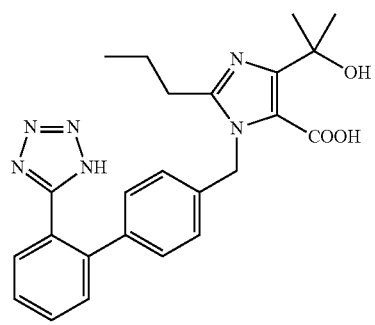
(10a)

by reacting a compound having the formula (9b):

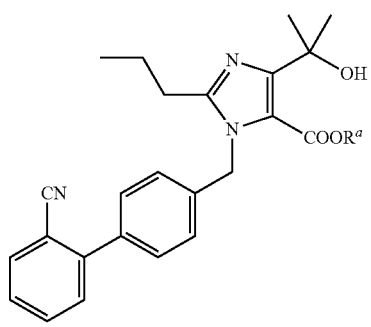
(9b)

(wherein $R^a$ represents a hydrogen atom or a $C_1$-$C_4$ alkyl group) with an inorganic azide salt having the formula $M(N_3)_n$ (wherein M represents an alkali metal or an alkaline earth metal, and n represents 1 or 2) in an aromatic hydrocarbon in the presence of a cyclic amine salt,
and hydrolyzing the resulting compound.

17. The production method according to claim 16, wherein $R^a$ is an ethyl group.

18. The production method according to claim 16, wherein the inorganic azide salt is sodium azide.

19. The production method according to claim 16, wherein the cyclic amine salt is a hydrochloride or a hydrobromide of N-methylpyrrolidine, N-methylpiperidine, N,N-dimethylpiperazine, N-methylmorpholine, N-methylthiomorpholine, N-methylhomopiperidine or N,N-dimethylhomopiperazine.

20. The production method according to claim 16, wherein the cyclic amine salt is a hydrochloride or a hydrobromide of N-methylpiperidine, N,N-dimethylpiperazine, N-methylmorpholine or N-methylthiomorpholine.

21. The production method according to claim 16, wherein the cyclic amine salt is N-methylpiperidine hydrochloride, N,N-dimethylpiperazine dihydrochloride or N-methylmorpholine hydrochloride.

22. The production method according to claim 16, wherein $R^a$ is an ethyl group, the inorganic azide salt is sodium azide, and the cyclic amine salt is a hydrochloride or a hydrobromide of N-methylpyrrolidine, N-methylpiperidine, N,N-dimethylpiperazine, N-methylmorpholine, N-methylthiomorpholine, N-methylhomopiperidine or N,N-dimethylhomopiperazine.

23. The production method according to claim 16, wherein $R^a$ is an ethyl group, the inorganic azide salt is sodium azide, and the cyclic amine salt is N-methylpiperidine hydrochloride, N,N-dimethylpiperazine dihydrochloride or N-methylmorpholine hydrochloride.

24. A method for producing a compound having the formula (9):

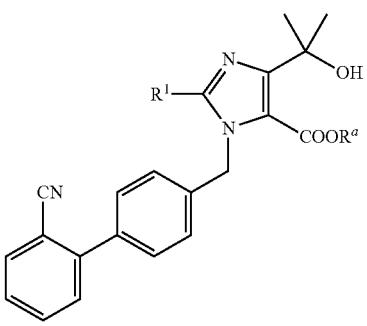
(9)

(wherein $R^1$ represents a hydrogen atom or a $C_1$-$C_4$ alkyl group, and $R^a$ represents a hydrogen atom or a $C_1$-$C_4$ alkyl group)
by reacting a compound having the formula (14):

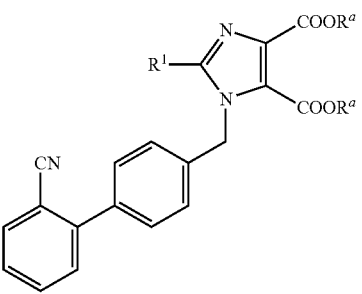
(14)

(wherein $R^1$ represents a hydrogen atom or a $C_1$-$C_4$ alkyl group, and $R^a$ represents a hydrogen atom or a $C_1$-$C_4$ alkyl group) with a compound having the formula MeMgX (wherein X represents a chloro group, a bromo group or an iodo group).

25. The production method according to claim 24, wherein $R_1$ is a 1-propyl group, and $R^a$ is an ethyl group.

26. The production method according to claim 24, wherein X is a chloro group.

27. The production method according to claim 24, wherein $R^1$ is a 1-propyl group, $R^a$ is an ethyl group and X is a chloro group.

28. A method for producing a compound having the formula (13a):

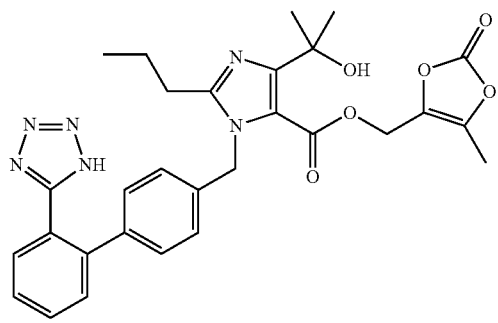

a part of the reaction steps of which comprises the production method according to claim 1.

29. A method for producing a compound having the formula (13a):

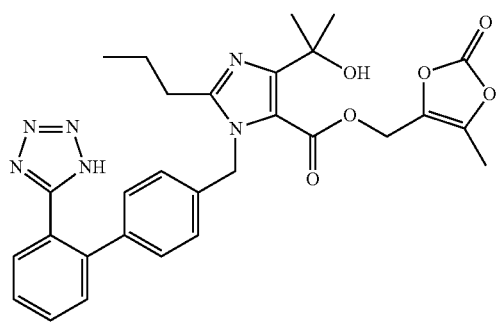

a part of the reaction steps of which comprises the production method according to claim 13.

30. A method for producing a compound having the formula (13a):

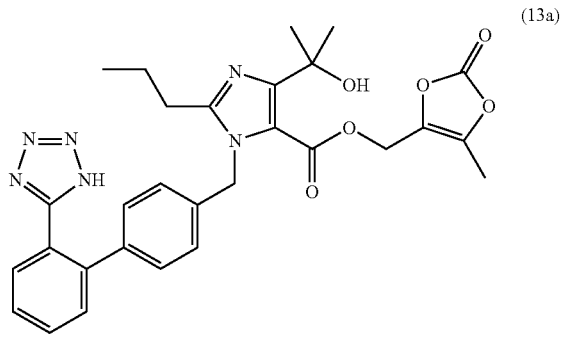 [SMILES: CCCc1nc(C(C)(C)O)c(C(=O)OCc2oc(=O)oc2C)n1Cc1ccc(-c2ccccc2-c2nnn[nH]2)cc1]

a part of the reaction steps of which comprises the production method according to claim 16.

31. A production method of a compound having the formula (13a):

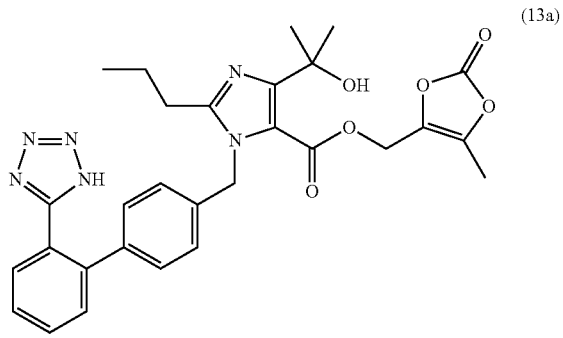 [SMILES: CCCc1nc(C(C)(C)O)c(C(=O)OCc2oc(=O)oc2C)n1Cc1ccc(-c2ccccc2-c2nnn[nH]2)cc1]

a part of the reaction steps of which comprises the production method according to claim 24.

* * * * *